(12) United States Patent
Diulgheroff et al.

(10) Patent No.: US 8,846,926 B2
(45) Date of Patent: Sep. 30, 2014

(54) FORMS OF TIOTROPIUM BROMIDE AND PROCESSES FOR PREPARATION THEREOF

(75) Inventors: Nicola Diulgheroff, Turin (IT); Francesca Scarpitta, Ivrea (IT); Alessandro Pontiroli, Milan (IT); Adrienne Kovacsne-Mezei, Debrecen (HU); Judith Aronhime, Rehovot (IL); Alexandr Jegorov, Dobra Voda (CZ)

(73) Assignee: Sicor Inc., Irvine, CA (US)

(*) Notice: Subject to any disclaimer, the term of this patent is extended or adjusted under 35 U.S.C. 154(b) by 0 days.

(21) Appl. No.: 13/339,042

(22) Filed: Dec. 28, 2011

(65) Prior Publication Data

US 2012/0108625 A1 May 3, 2012

Related U.S. Application Data

(62) Division of application No. 11/643,001, filed on Dec. 19, 2006, now Pat. No. 8,163,913.

(60) Provisional application No. 60/752,672, filed on Dec. 19, 2005, provisional application No. 60/754,530, filed on Dec. 27, 2005, provisional application No. 60/761,437, filed on Jan. 23, 2006, provisional application No. 60/774,051, filed on Feb. 15, 2006, provisional application No. 60/780,310, filed on Mar. 7, 2006, provisional application No. 60/832,189, filed on Jul. 20, 2006, provisional application No. 60/851,223, filed on Oct. 12, 2006, provisional application No. 60/852,740, filed on Oct. 18, 2006.

(51) Int. Cl.
*C07D 491/08* (2006.01)
*C07D 451/12* (2006.01)
*C07D 451/10* (2006.01)

(52) U.S. Cl.
CPC ............ *C07D 451/12* (2013.01); *C07D 451/10* (2013.01)
USPC ........................................... 546/91; 514/291

(58) Field of Classification Search
USPC ............................................ 514/291; 546/91
See application file for complete search history.

(56) References Cited

U.S. PATENT DOCUMENTS

| | | | |
|---|---|---|---|
| 5,610,163 | A | 3/1997 | Banholzer et al. |
| 6,608,055 | B2 | 8/2003 | Sieger et al. |
| 6,627,646 | B2 | 9/2003 | Bakale et al. |
| 6,777,423 | B2 | 8/2004 | Banholzer et al. |
| 7,968,717 | B2 | 6/2011 | Pfrengle et al. |
| 2002/0110529 | A1 | 8/2002 | Bechtold-Peters et al. |
| 2005/0096341 | A1 | 5/2005 | Banholzer et al. |
| 2005/0143410 | A1 | 6/2005 | Pfrengle et al. |
| 2006/0246009 | A1 | 11/2006 | Morissette et al. |

FOREIGN PATENT DOCUMENTS

| | | |
|---|---|---|
| CN | 1634921 | 7/2005 |
| EP | 2 085 396 | 8/2009 |
| IN | 1846/CHE/2007 | 8/2007 |
| WO | WO 02/30928 | 4/2002 |
| WO | WO 02/015840 | 7/2002 |
| WO | WO 03/000026 | 1/2003 |
| WO | WO 03/078429 | 9/2003 |
| WO | WO 2004/054580 | 7/2004 |
| WO | WO 2004/058233 | 7/2004 |
| WO | WO 2005/042426 | 5/2005 |
| WO | WO 2005/042527 | 5/2005 |
| WO | WO 2006/117299 | 11/2006 |
| WO | WO 2006/117300 | 11/2006 |
| WO | WO 2008/058968 | 5/2008 |
| WO | WO 2011/015882 | 2/2011 |
| WO | WO 2011/015883 | 2/2011 |

OTHER PUBLICATIONS

Kirk-Othmer "crystallization" Kirkothmer Encyclopedia of Chem Tech. p. 95-147 (2002).*
Giron "Investigation of poly . . . " J. Thermal Ana. Cal. v.64, p. 37-60 (2001).*
Bernstein "Polymoltphidm in molrvulst . . . " p. 115-118, 272 (2002).*
Braga et al. "Making crystals . . . " Roy. Soc. Chem. Chem. Commun. p. 3635-3645 (2005).*
Davidovich et al. "Detection of poly . . . " Am. Pharm. Rev. 7(1) p. 10, 12, 14,16,100 (2004).*
Dean "Analytical Chem . . . " p. 10.24-10.26 (1993).*
Haleblian "Characterization of habits . . . " J. Phar. Sci. p. 1269-88 (1975).*
Invanisevic et al. "Uses of x-ray powder . . . " Pharm. Sci. Encyclopedia p. 1-42 (2010).*
Kirk-Othmer "Crystallization" Encycl. of Chem. Tech. v.8, p. 95-147 (2002).*
Seddon "Pseudopolym . . . " Crystal growth & design v.4(6) 1087 (2004).*
Tung et ak, "Polymorphism" Cryst. Org. Compounds , p. 49 (2009).*
Vippagunta et al. "Crystalline solids" adv. Drug. Del. Rev. v.48, p. 3-26 (2001).*
Giron "Investigation of . . . " J. Thermal Anal. Cal. v. 64, p. 37-60 (2001).*
Third Party Observation filed in European Patent Application 06847887.4; Observation filed Dec. 27, 2010.
European Patent Office Official Action in European Patent Application 06847887.4, subsequent to the 3rd Party Observation that was filed Dec. 27, 2010; Official Action issued Sep. 19, 2011.
Response filed (Dec. 15, 2011) by Applicants in European Patent Application 06847887.4, subsequent to the Official Action issued Sep. 19, 2011.
Third Party Observation filed in European Patent Application 06847887.4; Observation filed Feb. 6, 2012.

(Continued)

*Primary Examiner* — Celia Chang
(74) *Attorney, Agent, or Firm* — Baker Hostetler LLP

(57) ABSTRACT

This invention relates to novel crystalline forms of tiotropium bromide, processes for preparing them, and their use in pharmaceutical formulations.

6 Claims, 16 Drawing Sheets

(56) References Cited

OTHER PUBLICATIONS

European Patent Office Official Action in European Patent Application 06847887.4, subsequent to the 3rd Party Observation which was filed Feb. 6, 2012. Official Action issued May 2, 2012.
Japanese Office Action from JP 2008-538130 mailed Sep. 6, 2011.
Davidovich "Detection of polymorph . . . " Am. Pharm. Rev. 7(1) p. 10, 12, 14, 16, 100 (2004).
Muzaffar et al. "Polymorphism and drug availability" J. Phar. 1(1) 59-66 (1979).
Jain et al. "Polymorphism in pharmacy" Indian Drugs 23(g) 315-329 (1986).
Doelker et al. "Crystalline modification . . . " CA 138:209993 (2002).
Doelker et al. "Physicochemical behavior or active . . . " CA 132:325872 (2000).
Otsuka et al. "Effect of polymorphic . . . " Chem. Pharm. Bull, 47(6) 852-856 (1999).
US Pharmacopia #23 national formulary #18, p. 1843-1844 (1995).
Dean "Analytical chemistry handbook" p. 10.24-10.26 (1995).
Exhibit 1 (2010).
Teva Pharmaceutical Industries, "Tiotropium bromide Form V", Publication No. IPCOM000143595D, Nov. 2006.
Tiotropium Bromide samples were crystalized according to Example 11 of patent US 5,610,163, (1997).

* cited by examiner

FORMS OF TIOTROPIUM BROMIDE AND PROCESSES FOR PREPARATION THEREOF

CROSS-REFERENCE TO RELATED APPLICATIONS

This application is a divisional of U.S. patent application Ser. No. 11/643,001, filed Dec. 19, 2006, which claims the benefit of the filing date of U.S. Provisional Patent Application No. 60/752,672 filed Dec. 19, 2005; U.S. Provisional Patent Application No. 60/754,530 filed Dec. 27, 2005; U.S. Provisional Patent Application No. 60/761,437 filed Jan. 23, 2006; U.S. Provisional Patent Application No. 60/774,051 filed on Feb. 15, 2006; U.S. Provisional Patent Application No. 60/780,310 filed Mar. 7, 2006; U.S. Provisional Patent Application No. 60/832,189 filed Jul. 20, 2006; U.S. Provisional Patent Application No. 60/851,223 filed Oct. 12, 2006; and U.S. Provisional Patent Application No. 60/852,740 filed Oct. 18, 2006, the disclosures of which are hereby incorporated herein by reference.

BACKGROUND OF THE INVENTION

Tiotropium bromide is an anticholinergic with specificity for muscarinic receptors. It therefore provides therapeutic benefit in the treatment of asthma or chronic obstructive pulmonary disease ("COPD").

The chemical name of Tiotropium bromide is (1α,2β,4β,5α,7β)-7-[(hydroxydi-2-thienylacetyl)oxy]-9,9-dimethyl-3-oxa-9-azoniatricyclo[3.3.1.0]nonane bromide or 6β,7β-epoxy-3β-hydroxy-8-methyl-1αH,5αH-tropanium bromide, di-2-thienylglycolate, and it has the following structure:

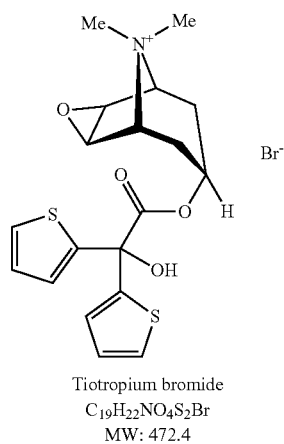

Tiotropium bromide
$C_{19}H_{22}NO_4S_2Br$
MW: 472.4

Tiotropium bromide is available commercially as SPIRIVA® HandiHaler®, available from Boehringer Ingelheim, in which it is present as the monohydrate form.

The preparation and crystallization of Tiotropium bromide from acetone and methanol is disclosed in U.S. Pat. No. 5,610,163, providing a product having a melting point of 217-218° C.

Crystalline forms of Tiotropium bromide have also been reported in various publications, such as U.S. Pat. No. 6,777,423, which describes a crystalline Tiotropium bromide monohydrate, U.S. Pat. No. 6,608,055, which describes a crystalline form of Tiotropium bromide anhydrate, WO 2005/042527 which describes another crystalline form of anhydrous Tiotropium bromide, and Publication No. IPCOM000143595D which describes a crystalline dichloromethane solvate of Tiotropium bromide.

The occurrence of different crystal forms (polymorphism) is a property of some molecules and molecular complexes. A single molecule, like the Tiotropium bromide in the above formula, may give rise to a variety of solids having distinct physical properties like melting point, X-ray diffraction pattern, infrared absorption fingerprint and NMR spectrum. The differences in the physical properties of polymorphs result from the orientation and intermolecular interactions of adjacent molecules (complexes) in the bulk solid. Accordingly, polymorphs are distinct solids sharing the same molecular formula, yet the polymorphs have distinct advantageous and/or disadvantageous physical properties compared to other forms in the polymorph family. One of the most important physical properties of pharmaceutical polymorphs is their solubility in aqueous solution.

The discovery of new crystalline polymorphic forms of a drug enlarges the repertoire of materials that a formulation scientist has available with which to design a pharmaceutical dosage form of a drug with a targeted release profile and/or other desired characteristics. Therefore, there is a need to find additional crystalline forms of Tiotropium bromide.

Similar advantages can come from new solvates which may lead to other polymorphs, may provide a better way to produce still other forms or solvates, or may provide processing advantages.

SUMMARY OF THE INVENTION

In one embodiment, the present invention provides a crystalline form of Tiotropium bromide, designated Form 1, characterized by a powder XRD pattern having peaks at about 8.7, 15.3, 15.5 and 25.3±0.2 degrees 2-theta.

In another embodiment, the present invention provides a process for preparing form 1 of Tiotropium bromide comprising crystallizing Tiotropium bromide from a mixture comprising methanol and acetone having a ratio of about 1/3 (vol/vol).

In yet another embodiment, the present invention provides a crystalline form of Tiotropium bromide, designated Form 2, characterized by a powder XRD pattern having peaks at about 23.1, 23.6, 24.1, 30.1 and 30.3±0.2 degrees 2-theta.

In one embodiment, the present invention provides a process for preparing form 2 of Tiotropium bromide comprising crystallizing Tiotropium bromide from a mixture comprised of methanol and acetone at a ratio of about 1/1 or about 3/1 (vol/vol).

In another embodiment, the present invention provides a crystalline form of Tiotropium bromide characterized by a powder XRD pattern having peaks at about 27.7, 27.8, 30.3 and 30.5±0.2 degrees 2-theta. This form can be designated as Form 6.

In yet another embodiment, the present invention provides a process for preparing Form 6 of Tiotropium bromide by a process comprising crystallizing Tiotropium bromide from a mixture comprising acetic acid, methanol, and heptane.

In one embodiment, the present invention provides a crystalline form of Tiotropium bromide, designated Form 7, characterized by a powder XRD pattern having peaks at about 8.8, 9.0, 11.7 and 17.7±0.2 degrees 2-theta.

In another embodiment, the present invention provides a process for preparing Form 7 of Tiotropium bromide is prepared by a process comprising crystallizing Tiotropium bromide from a mixture comprising a solvent mixture comprising of acetic acid and acetonitrile, and anti-solvent comprising of diisopropylether.

In yet another embodiment, the present invention provides a crystalline form of Tiotropium bromide, designated Form 8, characterized by a powder XRD pattern having peaks at about 16.2, 16.5, 28.0, and 28.3±0.2 degrees 2-theta.

In one embodiment, the present invention provides n-propanol solvate of Tiotropium bromide.

In another embodiment, the present invention provides a crystalline hemi-n-propanol solvate of Tiotropium bromide, designated Form 9.

In another embodiment, the present invention provides hemi-n-propanol solvate, designated Form 9, characterized by a single crystal XRD with the following data: monoclinic crystal system; space group of Pc, (No. 7); unit cell parameters: a, b, c: 13.4245, 12.0419, 13.6027 [Å], respectively, and alpha, beta, gamma: 90, 103.818, 90 [deg], respectively, and volume of: 2135.3 [Å$^3$], Z of 4 for formula $C_{20.5}H_{26}BrNO_{4.5}S_2$; and calculated density D of 1.53 [g/cm$^3$]. The said hemi-n-propanol solvate form may be also substantially identified by the calculated PXRD depicted in FIG. 10.

In yet another embodiment, the present invention provides a process for preparing Tiotropium bromide Form 9 by crystallizing tiotropium bromide from n-propanol at isothermal conditions.

In one embodiment, the present invention provides crystalline form of Tiotropium bromide, designated Form 11, characterized by a powder XRD pattern with peaks at about 20.2, 26.5, 28.0, and 31.2±0.2 degrees 2-theta.

In another embodiment, the present invention provides a crystalline hemi-n-propanol solvate of Tiotropium bromide, designated Form 12, characterized by a powder XRD pattern having peaks at about 20.9, 21.1, 21.4 and 34.4±0.1 degrees 2-theta.

In yet another embodiment, the present invention provides a process for preparing Tiotropium bromide Form 12 by providing a solution of Tiotropium bromide in n-propanol, and cooling to a temperature of about 55° C. to about 25° C. to obtain a suspension.

In another embodiment, the present invention provides amorphous Tiotropium bromide.

In another embodiment, the present invention provides a process for preparing the amorphous form of Tiotropium bromide by a process comprising lyophilizing a solution of Tiotropium bromide in water, t-butanol, methanol or mixtures thereof.

In yet another embodiment, the present invention offers a process for producing the monohydrate form of Tiotropium bromide, characterized by PXRD with peaks at 8.9, 11.9, 13.5, 14.8, 16.7, 17.5, 20.3, 23.6, 24.1, and 26.9± degrees 2-theta by a process comprising providing a mixture of Tiotropium bromide in water.

In yet another embodiment, the present invention provides micronized forms of Tiotropium bromide, designated 1, 2, 6, 7, 8, 9, 11, and amorphous.

In one embodiment, the present invention provides a process for preparing a crystalline form of Tiotropium bromide, designated form 3, characterized by a powder XRD pattern with peaks at about 9.82, 10.91, 13.45, 15.34, 17.93, 19.71, 20.90, and 21.45±0.2 degrees 2-theta, by a process comprising crystallizing Tiotropium bromide from a mixture comprising methanol and acetone at a ratio of about 3/1 (vol/vol), respectively.

In another embodiment, the present invention provides a process for preparing a crystalline form of Tiotropium bromide, designated Form 4, characterized by a powder XRD pattern with peaks at about 9.92, 11.03, 13.41, 15.31, 18.10, 19.91, 20.94, and 21.41±0.2 degrees 2-theta by a process comprising crystallizing Tiotropium bromide from ethanol.

In yet another embodiment, the present invention provides a process for preparing a crystalline form of Tiotropium bromide characterized by PXRD pattern with peaks at about 9.86, 10.97, 13.28, 15.28, 18.04, 19.80, 20.71, 21.26±0.2 degrees 2-theta by a process comprising crystallizing Tiotropium bromide from isopropanol.

In yet another embodiment, the present invention provides a process for preparing a crystalline form of Tiotropium bromide, designated Form 10, characterized by a PXRD pattern with peaks at about 9.82, 10.88, 13.28, 15.27, 16.39, 17.96, 19.67, 20.71, and 21.30±0.2 degrees 2-theta by a process comprising crystallizing Tiotropium bromide from n-butanol.

In one embodiment, the present invention provides pharmaceutical formulations comprising at least one form of Tiotropium bromide, designated 1, 2, 6, 7, 8, 9, 11, or amorphous form, and a pharmaceutically acceptable excipient.

In another embodiment, the present invention provides a process for preparing pharmaceutical formulations comprising at least one form of Tiotropium bromide, designated 1, 2, 6, 7, 8, 9, 11, or amorphous form, and a pharmaceutically acceptable excipient.

In yet another embodiment, the present invention provides pharmaceutical formulations comprising at least one form of Tiotropium bromide, designated 1, 2, 3, 4, 6, 7, 8, 9, 10, 11, or amorphous form, prepared according to the processes of the present invention, and a pharmaceutically acceptable excipient.

In one embodiment, the present invention provides a process for preparing pharmaceutical formulations comprising at least one form of Tiotropium bromide, designated Forms 1, 2, 3, 4, 6, 7, 8, 9, 10, 11, or amorphous form, prepared according to the processes of the present invention, and a pharmaceutically acceptable excipient.

In another embodiment, the present invention provides pharmaceutical formulations comprising at least one form of micronized Tiotropium bromide, designated 1, 2, 6, 7, 8, 9, 11, or amorphous and a pharmaceutically acceptable excipient.

In yet another embodiment, the present invention provides a process for preparing pharmaceutical formulations comprising at least one form of micronized Tiotropium bromide, designated 1, 2, 6, 7, 8, 9, 11, or amorphous and a pharmaceutically acceptable excipient.

In one embodiment, the present invention provides pharmaceutical formulations comprising at least one form of micronized Tiotropium bromide, designated 1, 2, 3, 4, 6, 7, 8, 9, 10, 11 or amorphous prepared according to the processes of the present invention, and a pharmaceutically acceptable excipient.

In another embodiment, the present invention provides a process for preparing pharmaceutical formulations comprising at least one form of micronized Tiotropium bromide, designated Forms 1, 2, 3, 4, 6, 7, 8, 9, 10, 11, or amorphous, prepared according to the processes of the present invention, and a pharmaceutically acceptable excipient.

DETAILED DESCRIPTION

As used herein, the term "room temperature" refers to a temperature ranging from about 18° C. to about 25° C., preferably ranging from about 20° C. to about 22° C.

The crystallization process disclosed in U.S. Pat. No. 5,610,163 fails to teach how to crystallize Tiotropium bromide to consistently obtain the same crystalline form. Hence, the present invention not only provides different crystalline and amorphous Tiotropium bromide but also methods for preparation thereof.

As used herein, the term "solvate" refers a crystalline substance that includes any solvent other than water at levels of more than 1%.

Figure 1:
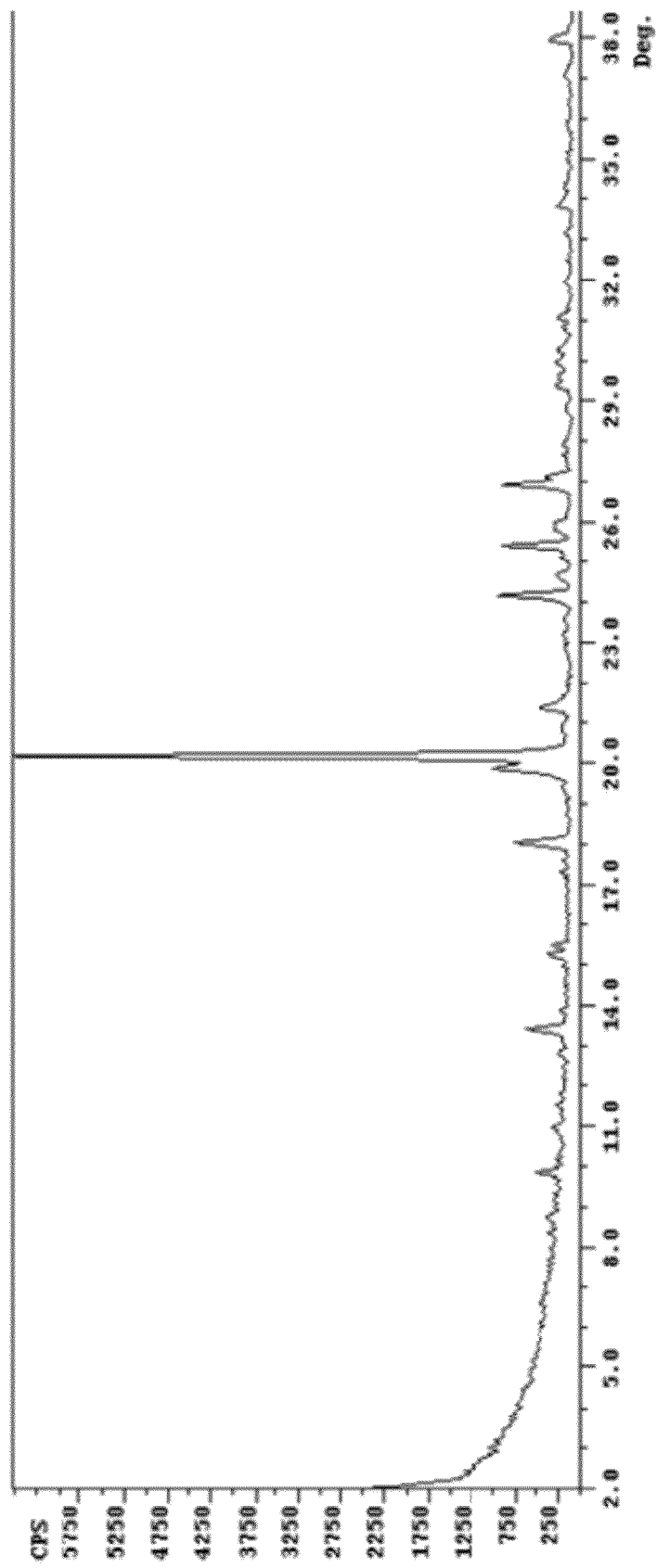
FIG. 1 shows the powder XRD pattern of Tiotropium bromide Form 1.

The present invention also provides crystalline Tiotropium bromide, designated Form 1, characterized by a powder XRD ("PXRD") pattern with peaks at about 8.7, 15.3, 15.5 and 25.3±0.2 degrees 2-theta. Form 1 may be further characterized by a powder XRD pattern with peaks at about 9.9, 13.3, 18.0, 20.2 and 24.2±0.2 degrees 2-theta. Form 1 may also be substantially identified by the PXRD pattern depicted in FIG. 1. Those skilled in the art would recognize that Form 1 may be characterized by other methods including, but not limited to, solid state NMR, FTIR, and Raman spectroscopy.

Form 1 may be a solvated form of Tiotropium bromide, preferably a methanolate. Crystalline Form 1 of Tiotropium bromide may be provided in a relatively pure form with no more than about 10% of any other form of Tiotropium bromide present, preferably with no more than about 5% of any other form of Tiotropium bromide as measured by PXRD. Preferably, crystalline Form 1 of Tiotropium bromide may be provided in a relatively pure form with no more than about 10% of Tiotropium bromide monohydrate, preferably with no more than about 5% of Tiotropium bromide monohydrate as measured by PXRD.

The said form 1 of Tiotropium bromide is prepared by a process comprising crystallizing Tiotropium bromide from a mixture comprising methanol and acetone having a ratio of about 1/3 (vol/vol).

The Tiotropium bromide, used for the above crystallization process, as well as for the following crystallization processes, described in this application, can be obtained by any method known to a skilled artisan. For example, it can be obtained by the method disclosed in U.S. Pat. No. 5,610,163.

The crystallization is done by a process comprising providing a solution of Tiotropium bromide in a mixture comprising methanol and acetone having a ratio of about 1/3 (vol/vol), and cooling the solution to obtain a suspension.

The solution of Tiotropium bromide is provided by combining Tiotropium bromide and a mixture comprising methanol and acetone having a ratio of about 1/3 (vol/vol), and heating. Preferably, the heating is done at temperature of about 50° C. to about 60° C., more preferably, to about 57° C.

Typically, the solution is cooled to induce precipitation of the crystalline form. Preferably, the solution is cooled to a temperature of about −6° C. to about −14° C., more preferably, to about −10° C. In a most preferred embodiment, the cooling is performed gradually so that the solution is cooled to a first temperature ranging from about 25° C. to about 20° C., preferably at a temperature of about 21° C., followed by cooling to a second temperature ranging from about −6° C. to about −14° C. Preferably, the gradual cooling is performed over a period of about 3 hours. Further cooling to a temperature of about −10° C. is, preferably, performed over a period of about 5 minutes.

The suspension may be maintained for at least about 3 hours, to increase the yield of the precipitated crystalline form.

The process for preparing form 1 may further comprise recovering the crystalline form from the suspension. The recovery may be done by any method known in the art, such as filtering, followed by drying under reduced pressure for at least 7 hours.

Figure 2:
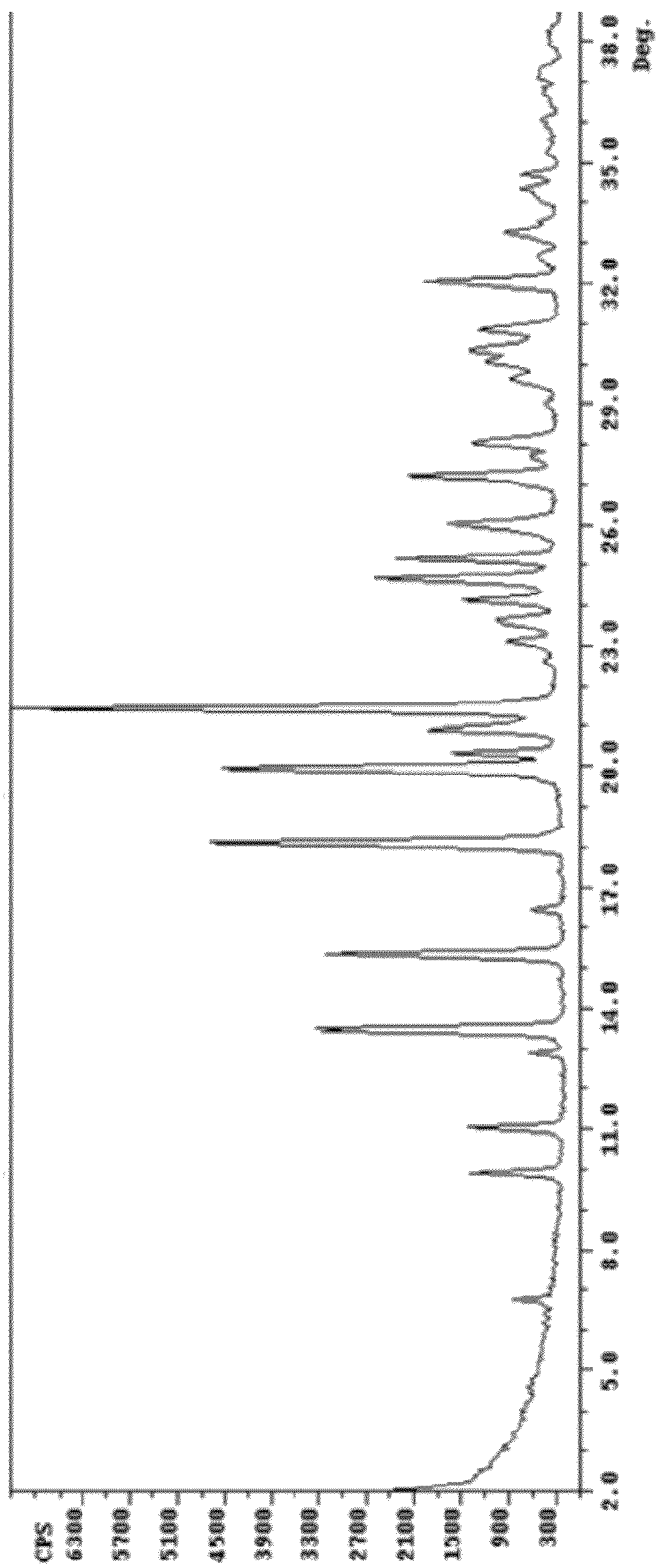
FIG. 2 shows the powder XRD pattern of Tiotropium bromide Form 2.
Figure 3:
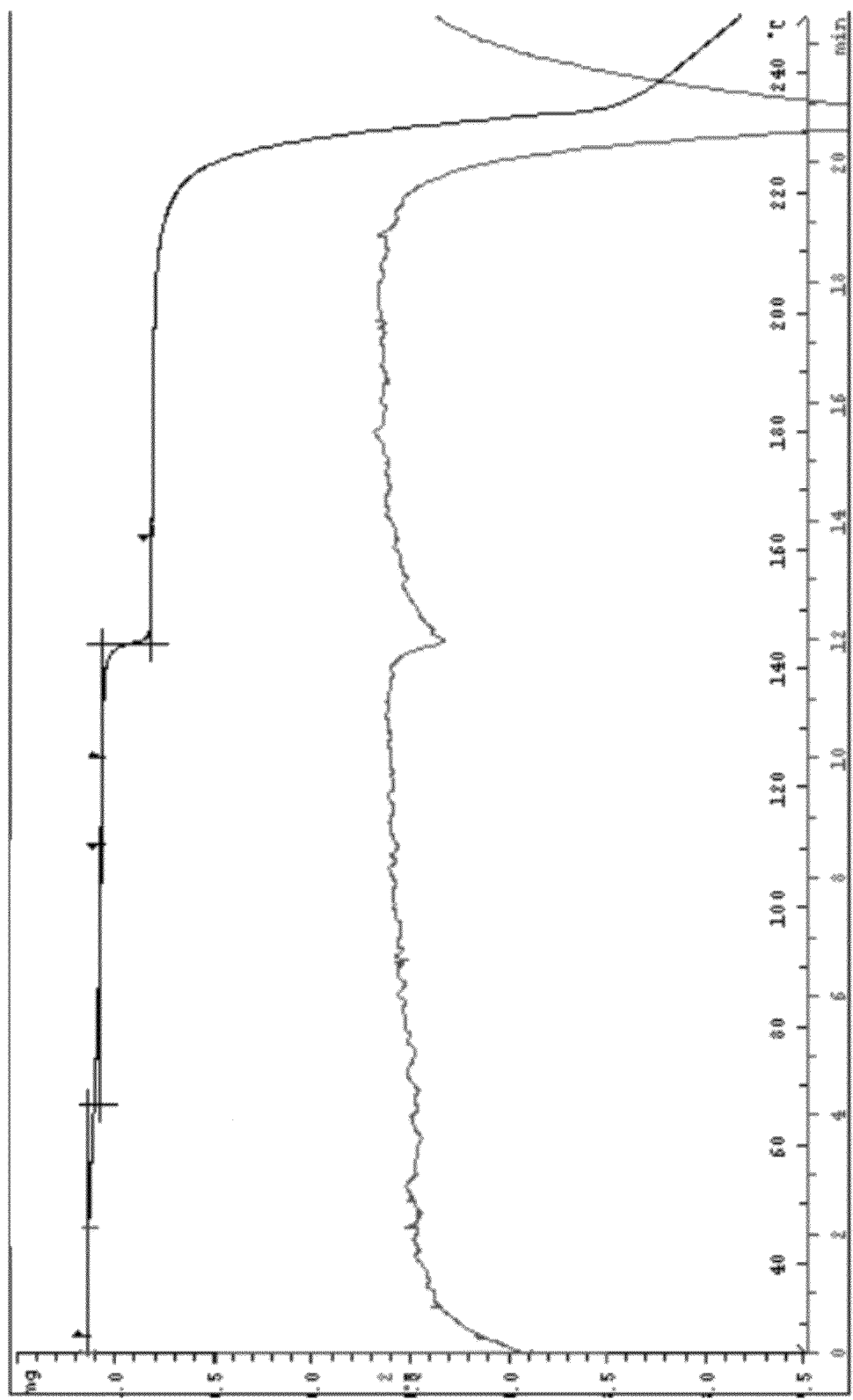
FIG. 3 shows the TGA curve of Tiotropium bromide Form 2.

The present invention further provides crystalline Tiotropium bromide, designated Form 2, characterized by a PXRD pattern with peaks at about 23.1, 23.6, 24.1, 30.1 and 30.3±0.2 degrees 2-theta. Form 2 may be further characterized by a PXRD pattern with peaks at about 9.9, 11.0, 13.4, 15.3, 18.1, 19.9, 21.4, 24.7, 25.2, 26.0 and 27.2±0.2 degrees 2-theta. Form 2 may be also substantially identified by the PXRD pattern depicted in FIG. 2. Form 2 may also be characterized by a weight loss step at about 160° C., of about 0.8% to about 2.3%, by thermal gravimetric analysis ("TGA"). Form 2 may be also substantially identified by the TGA curve depicted in FIG. 3. Form 2 may be also characterized by a differential scanning calorimetry ("DSC") thermogram having a first endothermic peak at about 144° C. and a second endothermic peak at about 228° C. Tiotropium bromide Form 2 may additionally be characterized by a melting point of about 207.6° C. Those skilled in the art would recognize that Form 2 may be characterized by other methods including, but not limited to, solid state NMR, FTIR, and Raman spectroscopy.

Form 2 may be a solvated form of Tiotropium bromide, preferably a methanolate solvate. Preferably, the amount of methanol as measured by gas chromatography ("GC") is about 4.1%. Crystalline Form 2 of Tiotropium bromide may be provided in a relatively pure form with no more than about 10% of any other form of Tiotropium bromide, preferably with no more than about 5% of any other form of Tiotropium bromide as measured by PXRD. Preferably, crystalline Form 2 of Tiotropium bromide may be provided in a relatively pure form with no more than about 10% of Tiotropium bromide monohydrate, preferably with no more than about 5% of Tiotropium bromide monohydrate, as measured by PXRD.

The said form 2 of Tiotropium bromide is prepared by a process comprising crystallizing Tiotropium bromide from a mixture comprising methanol and acetone at a ratio of about 1/1 or about 3/1 (vol/vol).

The crystallization is done by a process comprising providing a solution of Tiotropium bromide in a mixture comprising methanol and acetone having a ratio of about 1/1 or about 3/1 (vol/vol), and cooling the solution to obtain a suspension.

The solution of Tiotropium bromide is provided by combining Tiotropium bromide and a mixture comprising methanol and acetone having a ratio of about 1/1 to about 3/1 (vol/vol), and heating. Preferably, the heating is done to a temperature of about 50° C. to about 70° C., more preferably, to about 60° C.

Typically, the solution is cooled to induce precipitation of the crystalline form. Preferably, cooling is to a temperature of about 25° C. to about 20° C. Preferably, this temperature range is reached over a period of about 3 hours. The suspension may be maintained for at least about 2 hours, to increase the yield of the precipitated crystalline form.

The process for preparing form 2 may further comprise recovering the crystalline form from the suspension. The recovery may be done by any method known in the art, such as filtering, followed by drying under reduced pressure for at least 7 hours.

Figure 4:
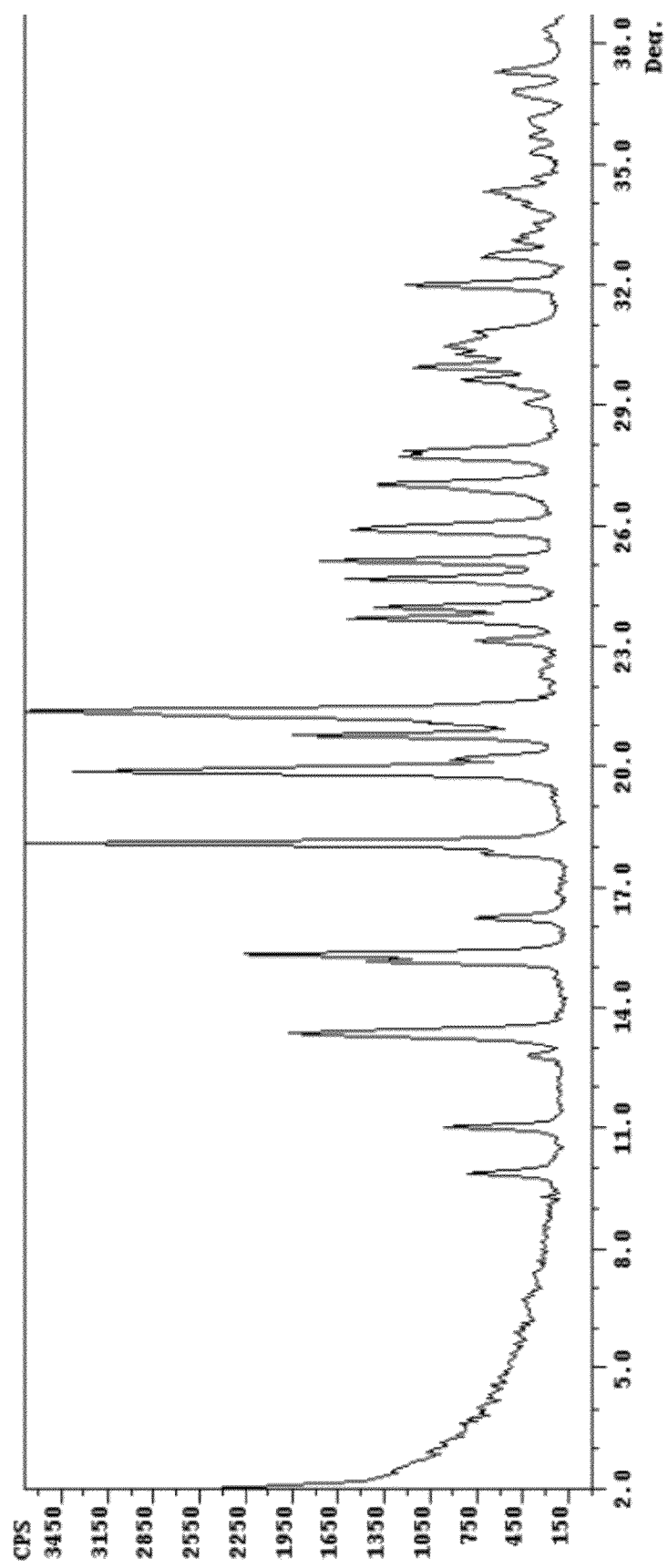
FIG. 4 shows the powder XRD pattern of Tiotropium bromide Form 6.
Figure 5:
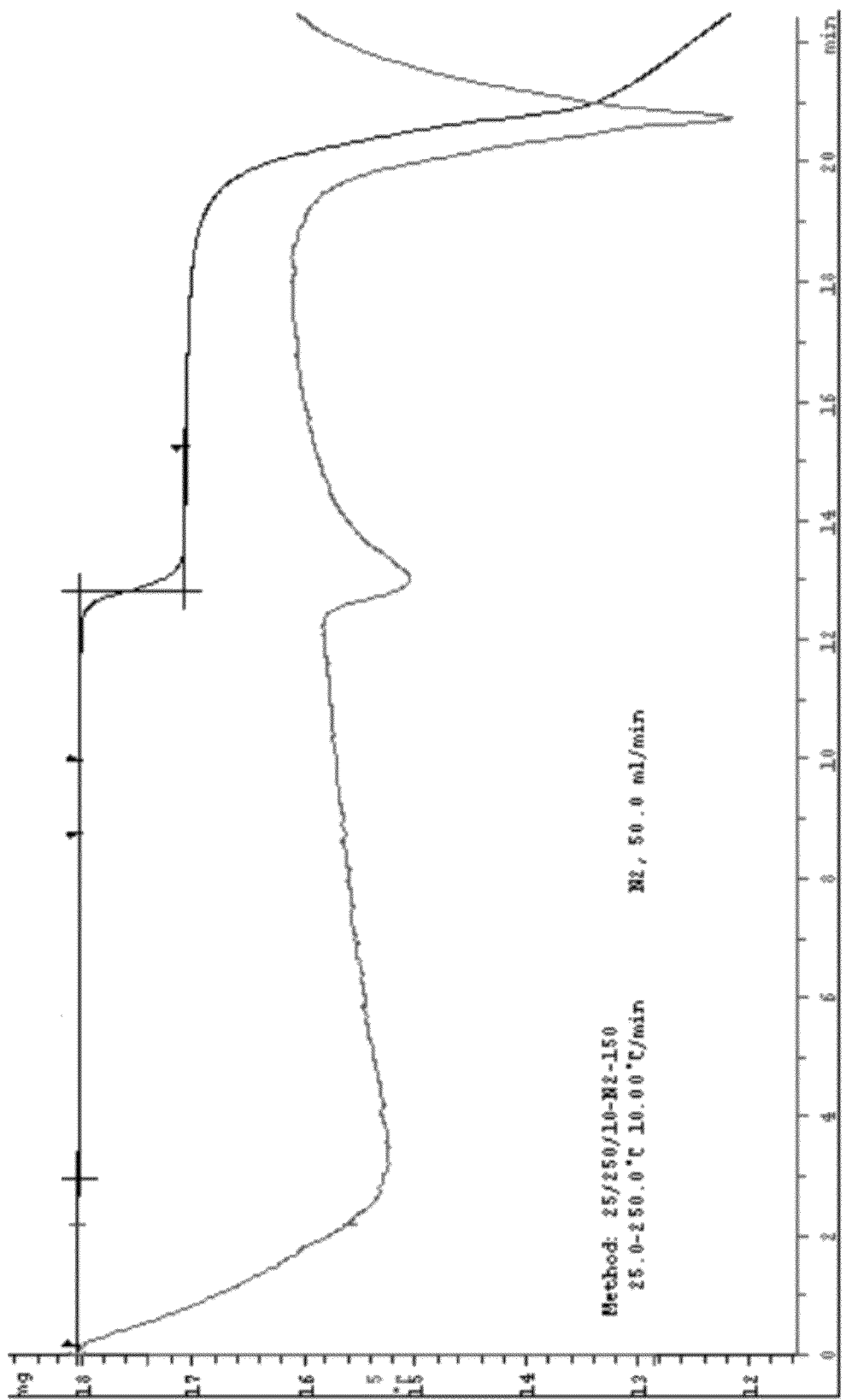
FIG. 5 shows the TGA curve of Tiotropium bromide Form 6.

The present invention further provides crystalline Tiotropium bromide characterized by a PXRD pattern with peaks at about 27.7, 27.8, 30.3 and 30.5±0.2 degrees 2-theta. This form can be designated as Form 6. This Form may be further characterized by a PXRD pattern with peaks at about 9.9, 11.0, 13.3, 15.3, 18.1, 19.9 and 21.3±0.2 degrees 2-theta. Form 6 may be also substantially identified by the PXRD pattern depicted in FIG. 4. Form 6 may be further characterized by weight loss step at about 160° C., of about 5.3% to about 5.7%, by TGA, wherein this level corresponds to the theoretical value of Tiotropium bromide hemi-acetic acid solvate. Form 6 may be also substantially identified by the TGA curve depicted in FIG. 5. Form 6 may be also characterized by a DSC thermogram having a first endothermic peak ranging from about 146° C. to about 150° C. and a second endothermic peak ranging from about 227° C. to about 228° C. Those skilled in the art would recognize that Form 6 may be characterized by other methods including, but not limited to, solid state NMR, FTIR, and Raman spectroscopy.

Form 6 may be a solvated form of Tiotropium bromide, preferably an acetic acid solvate, more preferably a hemi-acetic acid solvate. Preferably, the amount of acetic acid as measured by GC is of about 5.4%. Crystalline Form 6 of Tiotropium bromide may be provided in a relatively pure form with no more than about 10% of any other form of Tiotropium bromide, preferably with no more than about 5% of any other form of Tiotropium bromide, as measured by PXRD. Preferably, crystalline Form 6 of Tiotropium bromide may be provided in a relatively pure form with no more than about 10% of Tiotropium bromide monohydrate, preferably with no more than about 5% of Tiotropium bromide monohydrate, as measured by PXRD.

The form 6 of Tiotropium bromide is prepared by a process comprising crystallizing Tiotropium bromide from a mixture comprising acetic acid, methanol, and heptane.

The crystallization process comprises providing a first solution of Tiotropium bromide in a mixture comprising acetic acid and methanol; adding n-heptane to the first solution to obtain a second solution, and cooling the second solution to obtain a suspension.

The first solution of Tiotropium bromide is provided by combining Tiotropium bromide and a mixture comprising acetic acid and methanol, and heating.

The ratio of acetic acid and methanol in the first solution comprising acetic acid and methanol is, preferably, of about 7/1 to about 7/2 (vol/vol), respectively.

Preferably, the first mixture is heated to a temperature ranging from about 40° C. to about 50° C., more preferably, to a temperature of about 45° C. Preferably, the heating is performed over a period of about 1.5 hours.

Preferably, the addition of n-heptane to the first solution is done drop-wise. Preferably, the drop-wise addition is done over a period of at least about 20 to about 40 minutes. Preferably, the addition is done at a temperature ranging from about 40° C. to about 50° C., more preferably, at a temperature of about 45° C. After the addition of n-heptane, the obtained second solution is maintained at the above-referenced temperatures for about a half an hour to about one hour.

Typically, the second solution is cooled to induce precipitation of the crystalline form. The second solution is cooled, preferably to a temperature ranging from about 30° C. to about 20° C., more preferably, to a temperature ranging from about 30° C. to about 23° C. to, obtain a suspension. The suspension may be maintained for at least about 3 hours, to increase the yield of the precipitated crystalline form.

The process for preparing form 6 may further comprise recovering the crystalline form from the suspension. The recovery may be done by any method known in the art, such as filtering, washing the filtered form with n-heptane and drying.

Figure 6:
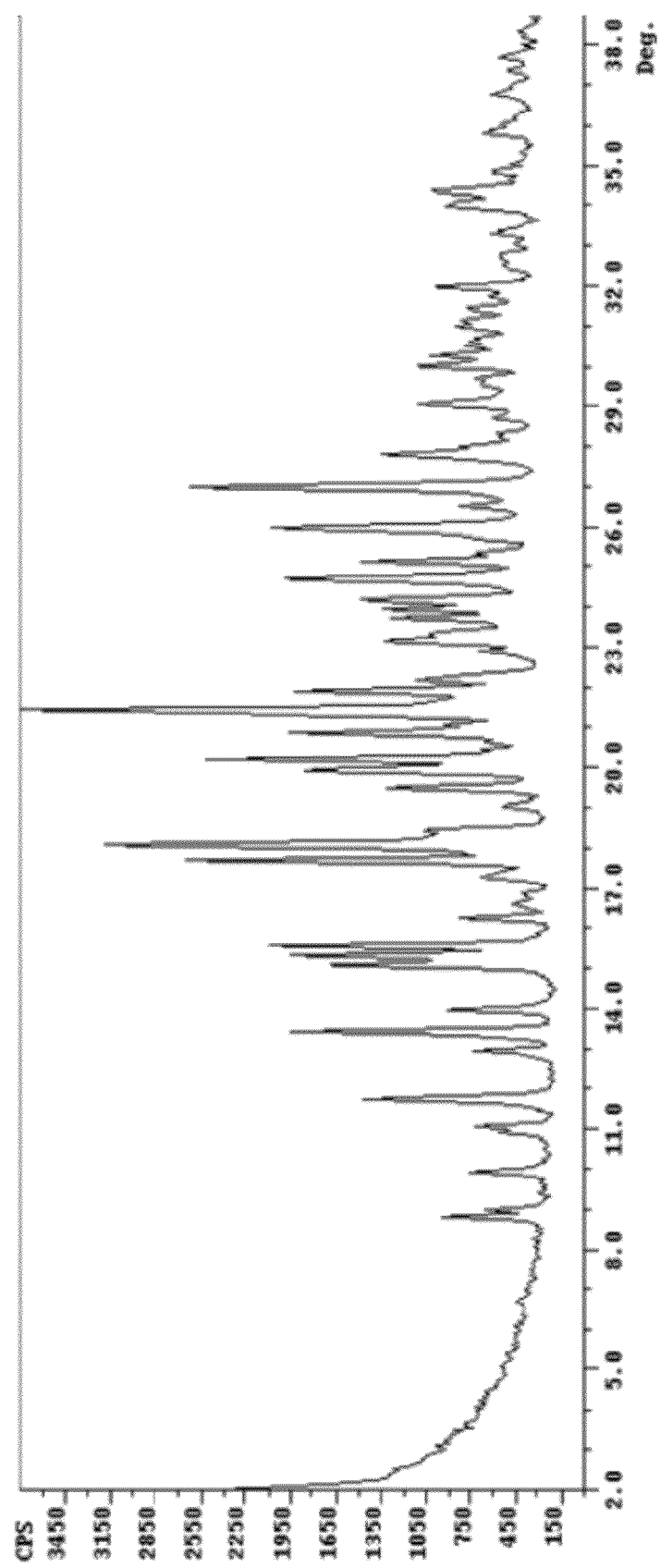
FIG. 6 shows the powder XRD pattern of Tiotropium bromide Form 7.
Figure 7:
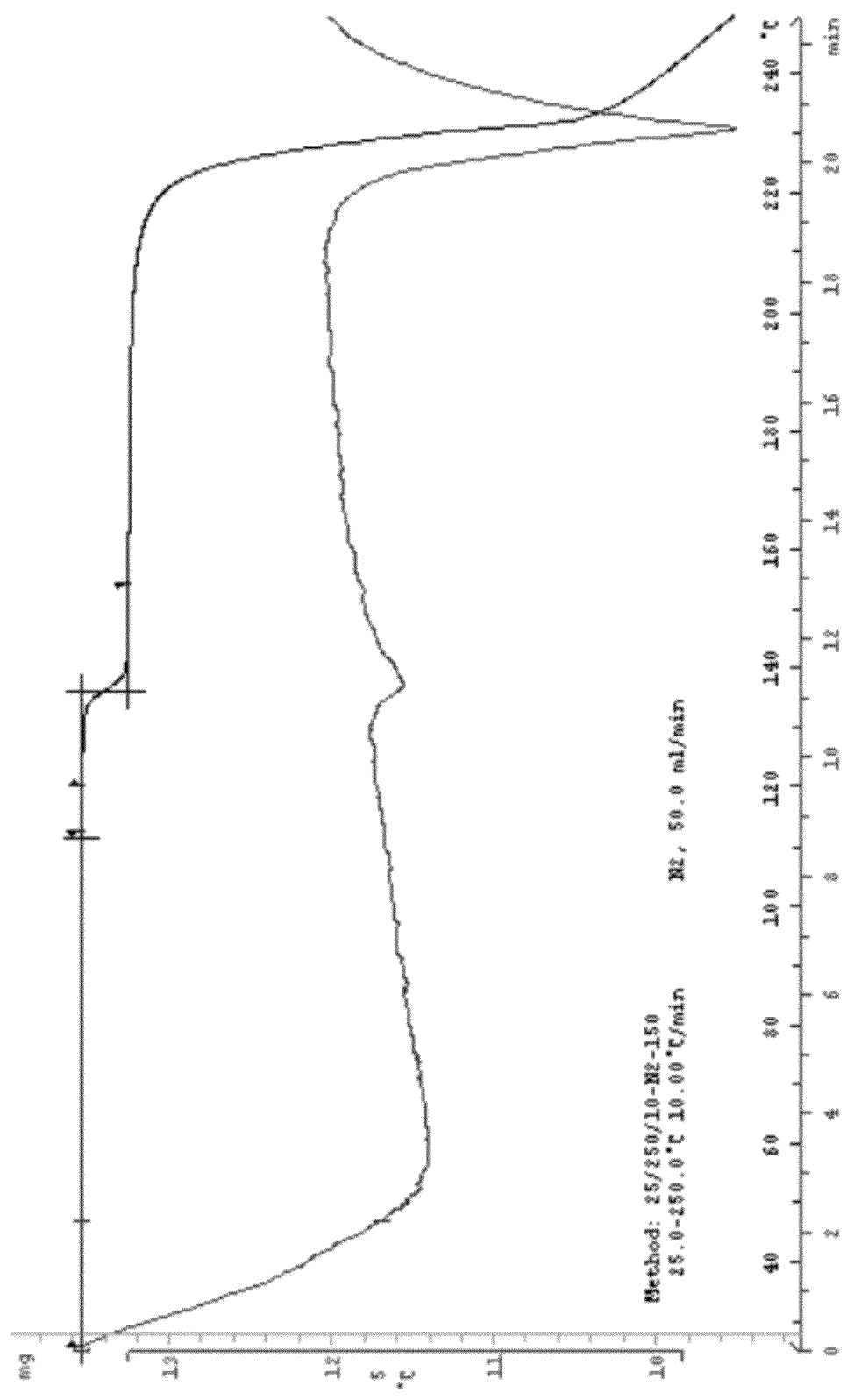
FIG. 7 shows the TGA curve of Tiotropium bromide Form 7.

The present invention further provides crystalline Tiotropium bromide, designated Form 7, characterized by a PXRD pattern with peaks at about 8.8, 9.0, 11.7 and 17.7±0.2 degrees 2-theta. Form 7 may be further characterized by a PXRD pattern with peaks at about 13.4, 15.1, 15.3, 15.6, 18.1 and 20.2±0.2 degrees 2-theta. Form 7 may be also substantially identified by the PXRD pattern depicted in FIG. 6. Form 7 may be further characterized by a weight loss of about 5.2%, by TGA. Form 7 may also be substantially identified by the TGA curve depicted in FIG. 7. Form 7 may also be characterized by a DSC thermogram having a first endothermic peak at about 136° C. and a second endothermic peak at about 228.0° C. Those skilled in the art would recognize that Form 7 may be characterized by other methods including, but not limited to, solid state NMR, FTIR, and Raman spectroscopy.

Form 7 may be a solvated form of Tiotropium bromide, preferably an acetic acid solvate. Preferably, the amount of acetic acid as measured by GC is of about 1.7%. Crystalline Form 7 of Tiotropium bromide may be provided in a relatively pure form with no more than about 10% of any other form of Tiotropium bromide, preferably with no more than about 5% of any other form of Tiotropium bromide, as measured by PXRD. Preferably, crystalline Form 7 of Tiotropium bromide may be provided in a relatively pure form with no more than about 10% of Tiotropium bromide monohydrate, preferably with no more than about 5% of Tiotropium bromide monohydrate, as measured by PXRD.

The said form 7 of Tiotropium bromide is prepared by a process comprising crystallizing Tiotropium bromide from a mixture comprising a solvent mixture comprising of acetic acid and acetonitrile, and anti-solvent comprising of diisopropylether.

The crystallization process comprises providing a solution of Tiotropium bromide in the said solvent, and adding Diisopropylether to the solution to obtain a suspension.

Preferably, the solution of Tiotropium bromide is provided by combining Tiotropium bromide and the said solvent, and heating.

The ratio of acetic acid and acetonitrile in the said solvent is, preferably, of about 1/4 to about 1/5 (vol/vol), respectively.

Preferably, heating is done to at a temperature ranging from about 40° C. to about 50° C. More preferably, the heating is performed at a temperature of about 45° C. Preferably, the heating is performed for a period of about 1.5 hours.

Preferably, the addition of diisopropylether to the solution is drop-wise, more preferably over at least about 15 minutes. Preferably, the addition is done at a temperature ranging from about 40° C. to about 50° C., more preferably, to a temperature of about 45° C. After the addition of Diisopropylether, the obtained suspension is maintained at the above-referenced temperatures for about an hour.

Typically the suspension is cooled to increase the yield of the precipitated product. Preferably, cooling is done to a temperature of from about 30° C. to about 20° C., more preferably, the solution is cooled to a temperature from about 30° C. to about 21° C. The cooling is done for a period of at least 3 hours.

The process for preparing form 7 may further comprise recovering the crystalline form from the suspension. The recovery may be done by any method known in the art, such as filtering, followed by washing the filtered form with Diisopropylether and drying.

Figure 8:
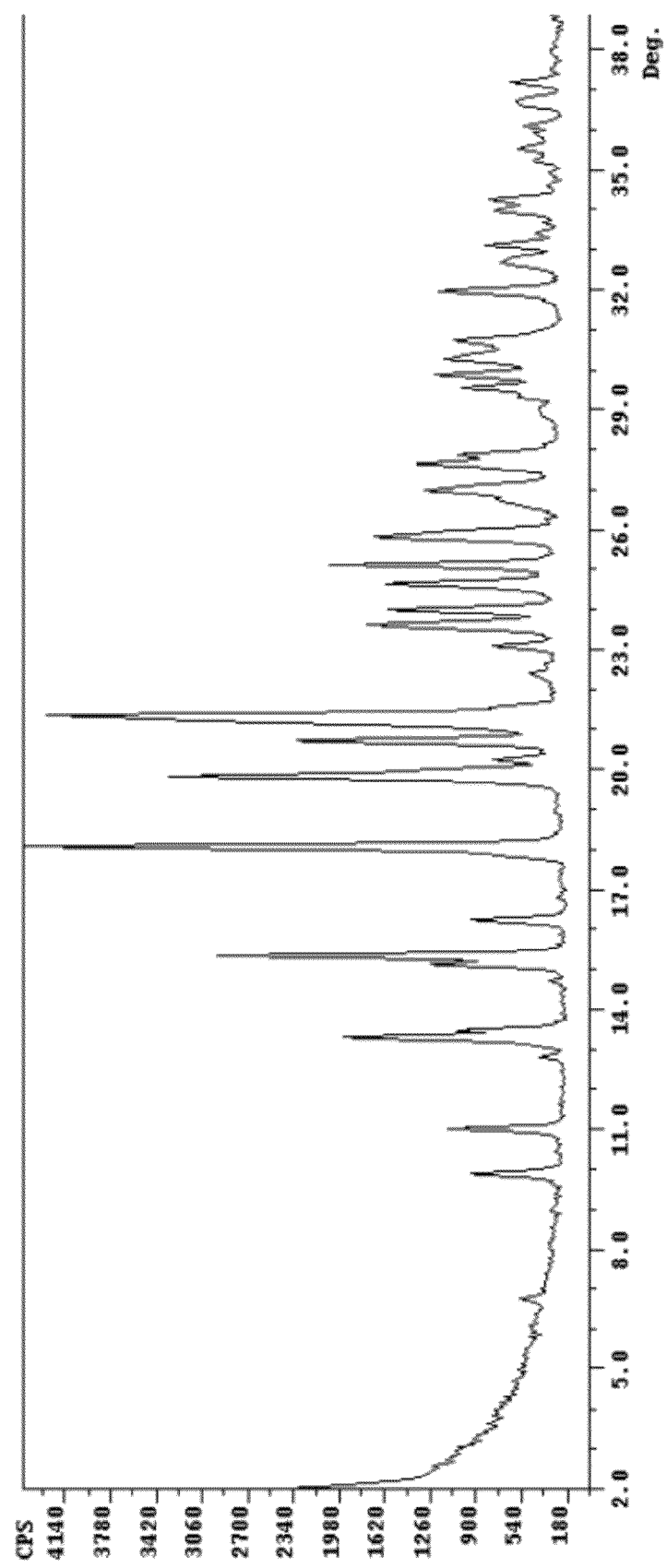
FIG. 8 shows the powder XRD pattern of Tiotropium bromide Form 8.
Figure 9:
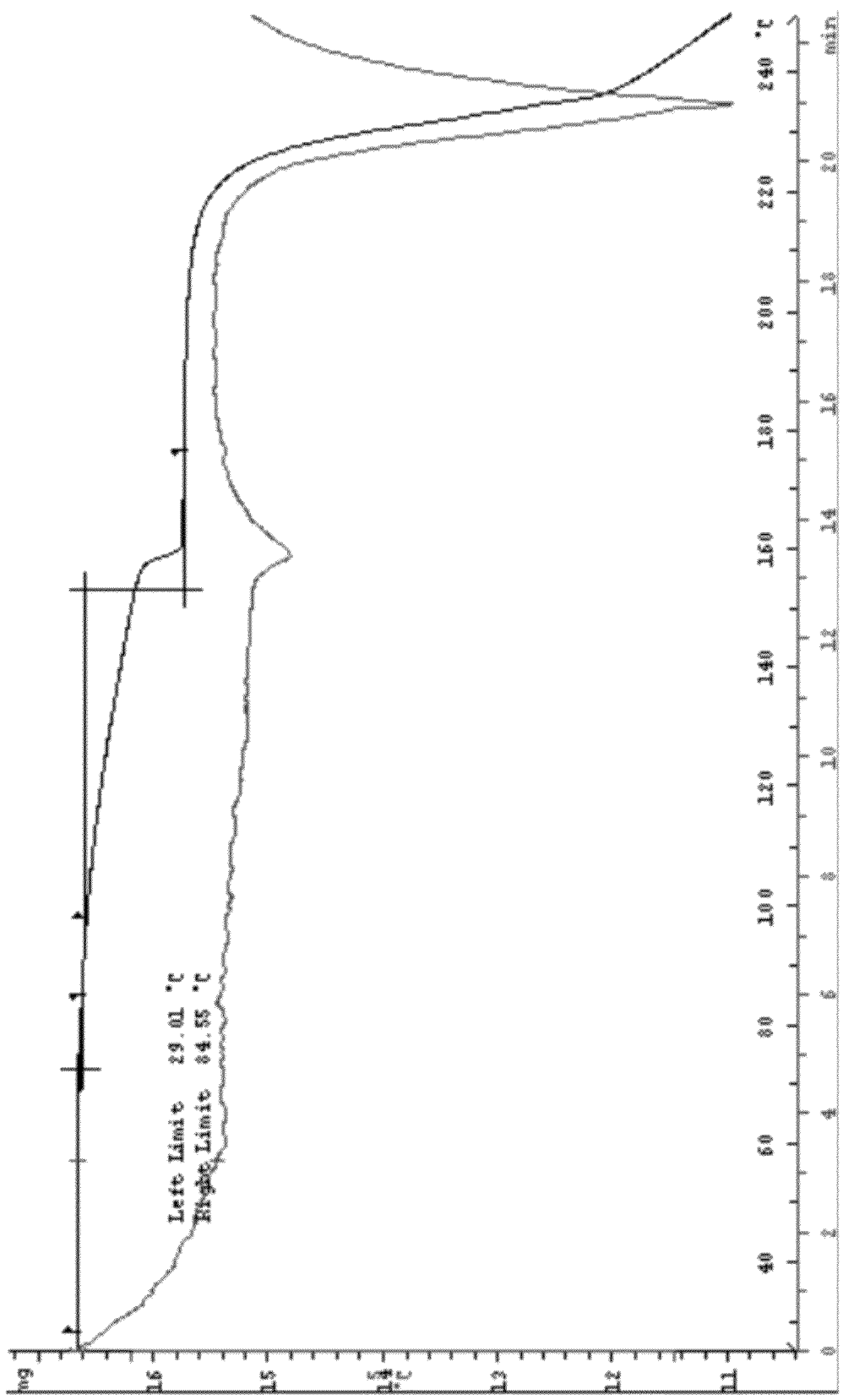
FIG. 9 shows the TGA curve of Tiotropium bromide Form 8.

The present invention provides crystalline Tiotropium bromide, designated Form 8, characterized by a PXRD pattern with peaks at about 16.2, 16.5, 28.0, and 28.3±0.2 degrees 2-theta. Form 8 may be further characterized by a PXRD pattern with peaks at about 9.9, 11.0, 13.4, 15.3, 17.9, 19.7, 20.9, and 21.4±0.2 degrees 2-theta. Form 8 may be also substantially identified by the PXRD pattern depicted in FIG. 8. Form 8 may be further characterized by weight loss of about 5.1%, by TGA. Form 8 may be also substantially identified by the TGA pattern depicted in FIG. 9. Form 8 may also be characterized by a DSC thermogram having a first endothermic peak at about 149° C. and a second endothermic peak at about 226° C. Those skilled in the art would recognize that Form 8 may be characterized by other methods including, but not limited to, solid state NMR, FTIR, and Raman spectroscopy.

Form 8 may be a solvated form of Tiotropium bromide, preferably alcoholate, and more preferably methanolate. Crystalline Form 8 of Tiotropium bromide may be provided in a relatively pure form with no more than about 10% of any other form of Tiotropium bromide, preferably with no more than about 5% of any other form of Tiotropium bromide, as measured by PXRD. Preferably, crystalline Form 8 of Tiotropium bromide may be provided in a relatively pure form with no more than about 10% of Tiotropium bromide monohydrate, preferably with no more than about 5% of Tiotropium bromide monohydrate, as measured by PXRD.

Crystalline form 8 of Tiotropium bromide is prepared by a process comprising crystallizing Tiotropium bromide from methanol.

The process comprises providing a solution of Tiotropium bromide in methanol, and cooling the solution to obtain a suspension.

Preferably, the solution of Tiotropium bromide in methanol is provided by combining Tiotropium bromide and methanol, and heating to obtain a solution. Preferably, heating is done to a temperature ranging from about 61° C. to about 65° C. More preferably, the heating is done at a temperature of about 63° C. Preferably, the heating is performed for a period of about 1 hour.

Typically, the solution is cooled to induce precipitation of the crystalline form. The solution is, preferably, cooled to a temperature ranging from about 27° C. to about 22° C. More preferably, the solution is cooled to a temperature of about 22° C. Reaching the above temperature is done over a period of at least about 2 hours.

The obtained suspension may be maintained for at least about 3.5 hours, to increase the yield of the precipitated product.

The process for preparing crystalline form 8 may further comprise recovering the crystalline form from the suspension. The obtained precipitate may be recovered from the suspension by any method known in the art, such as filtering, followed by washing the filtered form with methanol and drying.

The present invention also provides n-propanol solvate of Tiotropium bromide.

Figure 10:
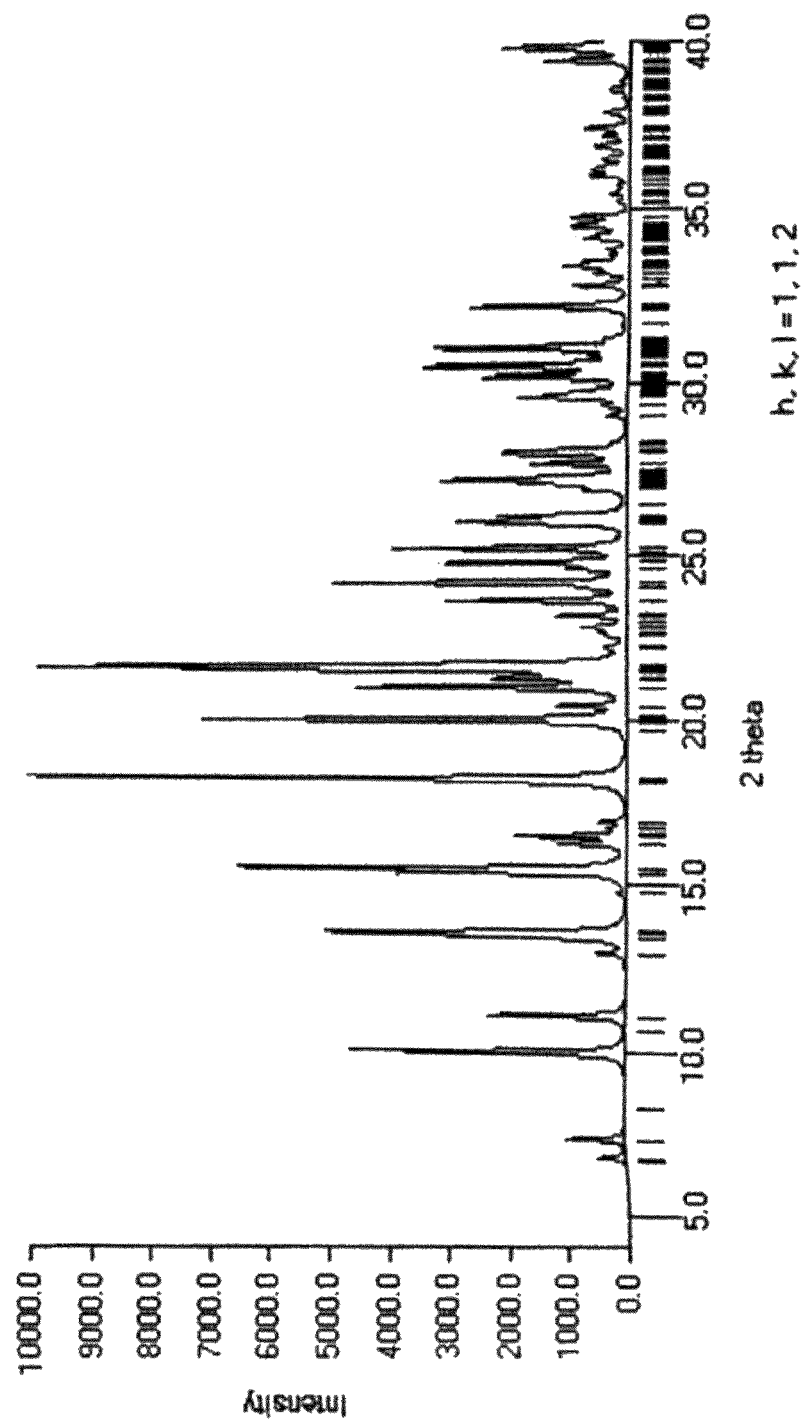
FIG. 10 shows the calculated powder XRD pattern of Tiotropium bromide Form 9.

The present invention also provides crystalline Tiotropium bromide hemi-n-propanol solvate substantially identified by the calculated PXRD pattern depicted in FIG. 10. The crystalline n-propanolate solvate may be further characterized by weight loss of about 5.9%, by TGA, wherein this level corresponds to the theoretical value of hemi-n-propanol solvate of Tiotropium bromide. The stiochiometric value of hemi-n-propanolate is 5.9%. Crystalline hemi-n-propanol solvate of Tiotropium bromide may be provided in a relatively pure form with no more than about 10% of any other form of Tiotropium bromide, preferably with no more than about 5% of any other form of Tiotropium bromide, as measured by PXRD. Preferably, hemi-n-propanol solvate of Tiotropium bromide may be provided in a relatively pure form with no more than about 10% of Tiotropium bromide monohydrate, preferably with no more than about 5% of Tiotropium bromide monohydrate, as measured by PXRD. Those skilled in the art would recognize that Form 9 may be characterized by other methods including, but not limited to, solid state NMR, FTIR, and Raman spectroscopy.

Figure 11:
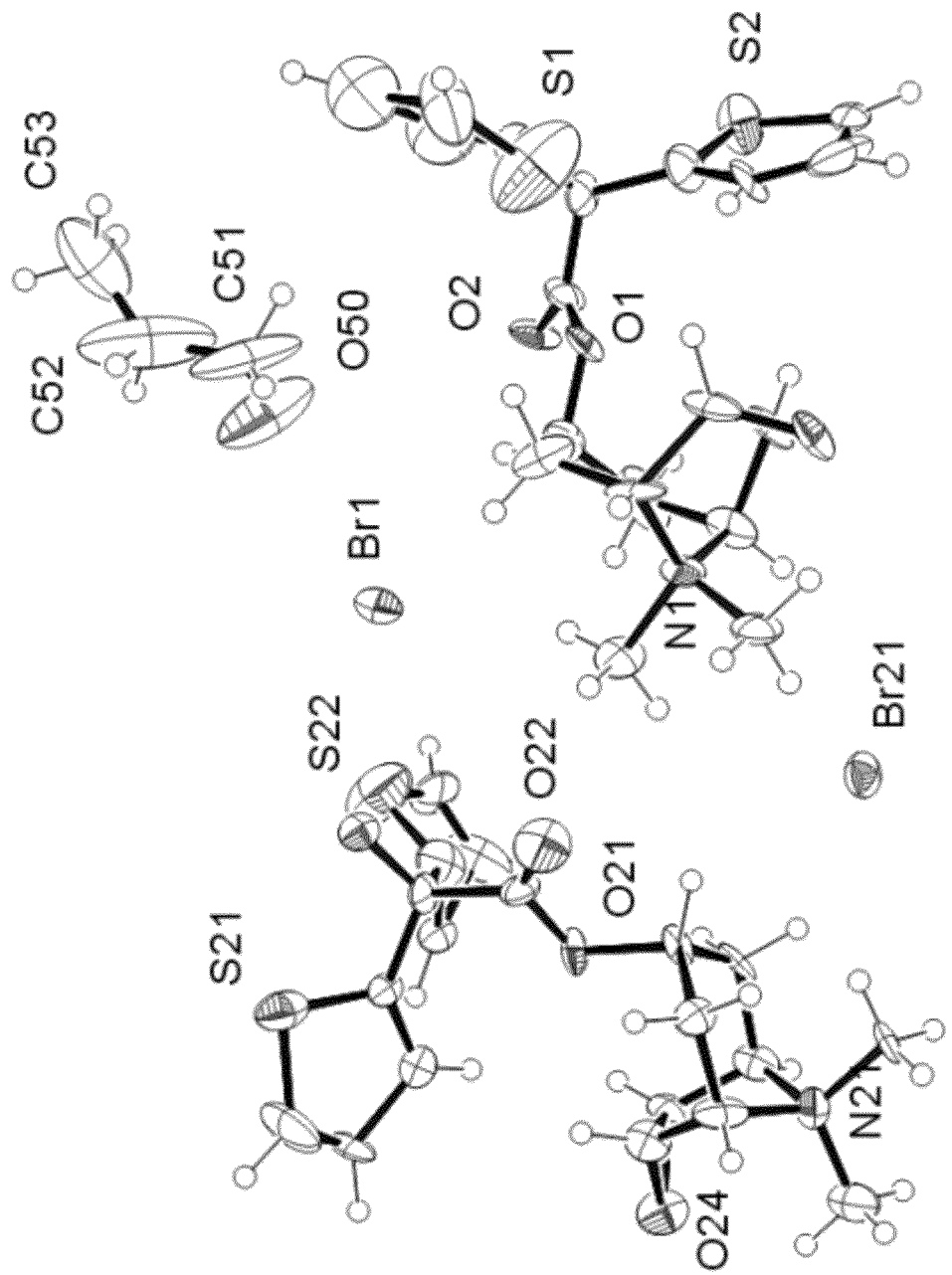
FIG. 11 shows the ORTEP view of Tiotropium bromide Form 9.

The present invention provides hemi-n-propanol solvate, designated Form 9, characterized by a single crystal XRD with the following data: monoclinic crystal system; space group of Pc, (No. 7); unit cell parameters: a, b, c: 13.42, 12.04, 13.60 [Å], respectively, and alpha, beta, gamma: 90, 103.8, 90 [deg], respectively, and volume of: 2135 [Å$^3$], Z of 4 for formula $C_{20.5}H_{26}BrNO_{4.5}S_2$; and calculated density D of 1.53 [g/cm$^3$]. The said hemi-n-propanol form may be also substantially identified by the ORTEP view depicted in FIG. 11.

The present invention provides a process for preparing Tiotropium bromide Form 9 characterized by a single crystal XRD with the following data: monoclinic crystal system; space group of Pc, (No. 7); unit cell parameters: a, b, c: 13.4245, 12.0419, 13.6027[Å], respectively, and alpha, beta, gamma: 90, 103.818, 90 [deg], respectively, and volume of: 2135.3 [Å$^3$], Z of 4 for formula $C_{20.5}H_{26}BrNO_{4.5}S_2$; and calculated density D of 1.53 [g/cm$^3$] by crystallizing tiotropium bromide from n-propanol at isothermal conditions.

Typically, the term "isothermal conditions" refers to constant temperature. Preferably, the isothermal condition for preparing form 9 is a temperature of 25° C.

The process comprises providing a solution of Tiotropium bromide in n-propanol, cooling the solution to a temperature of 25° C. to obtain a mixture, and maintaining the mixture at 25° C. for about 5 days.

Preferably, the solution of Tiotropium bromide in n-propanol is provided by combining Tiotropium bromide and n-propanol, and heating. The heating is done, preferably, to a temperature of from about 80° C. to about 100° C., more preferably, to 97° C.

Typically, the solution is cooled to induce precipitation of single crystals.

The process for preparing form 9 may further comprise recovering the crystalline form. The recovery may be done by any method known in the art, such as filtering, washing the filtered form and drying.

Figure 12:
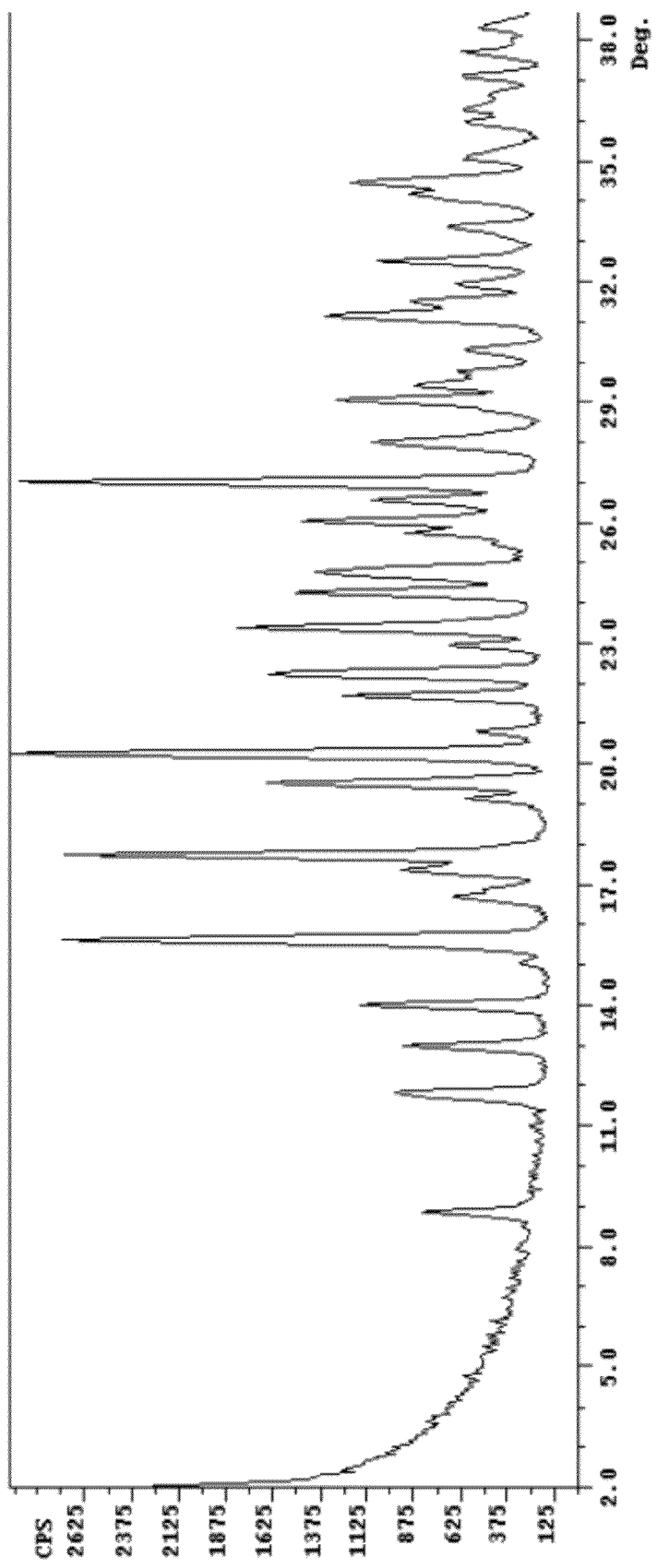
FIG. 12 shows the powder XRD pattern of Tiotropium bromide Form 11.
Figure 13:
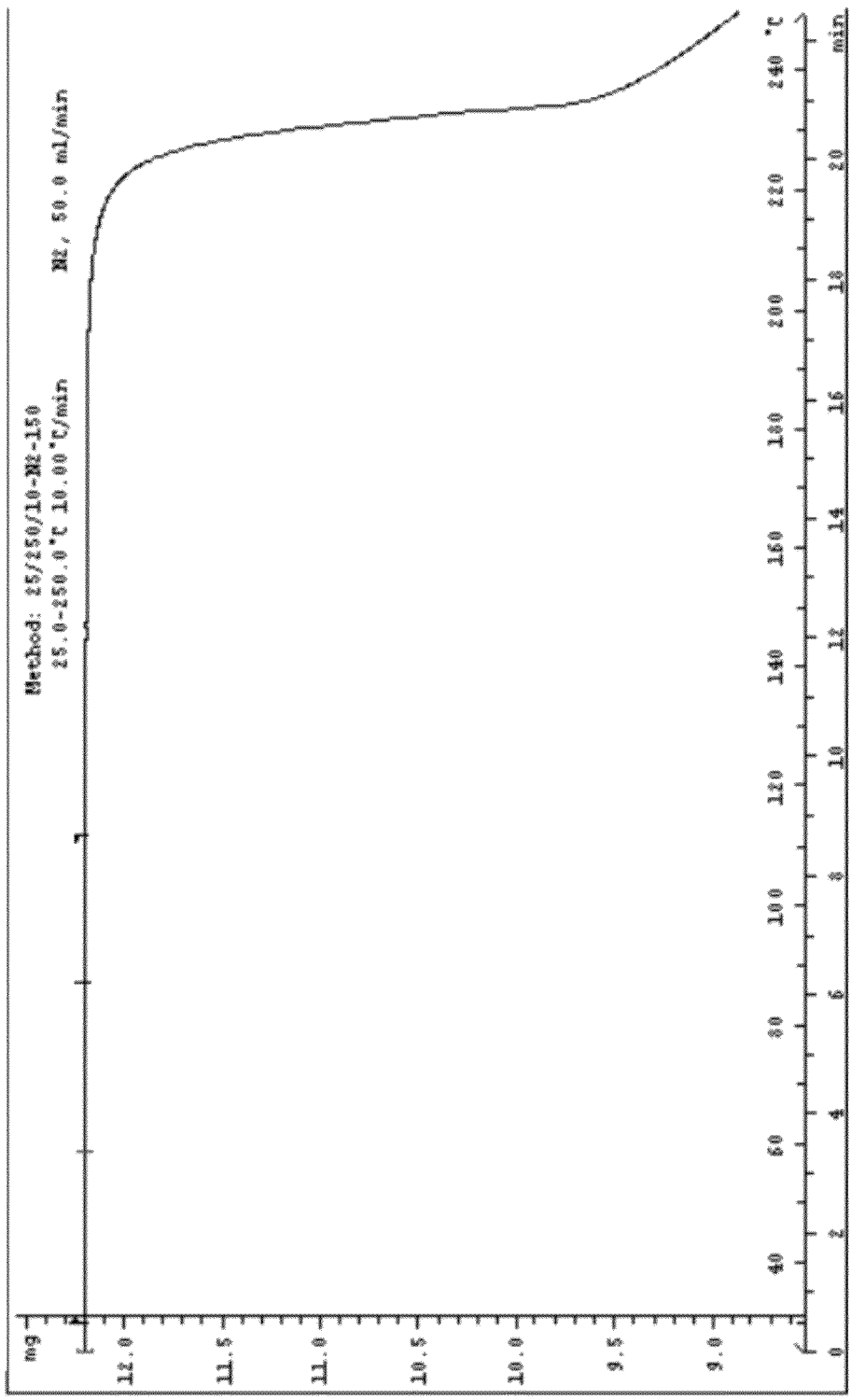
FIG. 13 shows the TGA curve of Tiotropium bromide Form 11.

The present invention provides crystalline form of Tiotropium bromide, designated Form 11, characterized by a PXRD pattern with peaks at about 20.2, 26.5, 28.0, and 31.2±0.2 degrees 2-theta. Form 11 may be further characterized by a PXRD pattern with peaks at about 8.9, 15.6, 17.7, 21.7, 23.4, and 24.3±0.2 degrees 2-theta. Form 11 may be also substantially identified by the PXRD pattern depicted in FIG. 12. Form 11 may be further characterized by weight loss of about <0.1%, by TGA. Form 11 may be also substantially identified by the TGA curve depicted in FIG. 13. Form 11 may be further characterized by a DSC thermogram having an endothermic peak at about 227° C. Those skilled in the art would recognize that Form 11 may be characterized by other methods including, but not limited to, solid state NMR, FTIR, and Raman spectroscopy.

Form 11 may be an anhydrous form of Tiotropium bromide. Crystalline Form 11 of Tiotropium bromide may be provided in a relatively pure form with no more than about 10% of any other form of Tiotropium bromide, preferably with no more than about 5% of any other form of Tiotropium bromide, as measured by PXRD. Preferably, crystalline Form of Tiotropium bromide may be provided in a relatively pure form with no more than about 10% of Tiotropium bromide monohydrate, preferably with no more than about 5% of Tiotropium bromide monohydrate, as measured by PXRD.

Crystalline form 11 of Tiotropium bromide is prepared by a process comprising heating any Tiotropium bromide solvate to a temperature ranging from about 160° C. to about 170° C.

Preferably, a Tiotropium bromide solvate is heated to a temperature of about 160° C. Preferably, the heating is done at for about 1 hour to about 2 hours, more preferably for about 1 hour.

The present invention provides a crystalline hemi-n-propanol solvate of Tiotropium bromide, designated Form 12, characterized by a powder XRD pattern having peaks at about 20.9, 21.1, 21.4 and 34.4±0.1 degrees 2-theta.

Form 12 may be further characterized by a PXRD pattern with peaks at about 9.9, 11.0, 13.5, 15.3, 18.1, 19.9, 20.9, 21.1, 21.4, 23.9, 25.1, 27.1, and 34.4±0.2 degrees 2-theta. Form 12 may be also substantially identified by the PXRD pattern depicted in FIG. 14. Form 12 may be further characterized by weight loss of about 5.9% at a temperature of about 125° C. to about 184° C., by TGA wherein this level corresponds to the theoretical value of hemi-n-propanol solvate of Tiotropium bromide. Form 12 may be also substantially identified by the TGA curve depicted in FIG. 15. Form 12 may be further characterized by a DSC thermogram having a first endothermic peak at 158° C., and a second endothermic peak at about 229° C. Those skilled in the art would recognize that Form 12 may be characterized by other methods including, but not limited to, solid state NMR, FTIR, and Raman spectroscopy.

Tiotropium bromide Form 12 is prepared by a process comprising providing a solution of Tiotropium bromide in n-propanol, and cooling to a temperature of about 55° C. to about 25° C. to obtain a suspension.

Preferably, the solution of Tiotropium bromide in n-propanol is provided by combining Tiotropium bromide and n-propanol, and heating. The heating is done, preferably, to a temperature of from about 80° C. to about 100° C., more preferably, to 97° C.

Typically, the solution is cooled to induce precipitation of the said crystalline form. The solution is cooled, preferably to a temperature of from about 55° C. to about 25° C. Preferably, the cooling is done gradually. The gradual cooling is done by reaching a temperature of about 55° C., and then further cooling to a temperature of about 25° C. to about 21° C. Preferably, reaching 55° C. is done over a period of about 4 hours. Preferably, reaching a temperature of about 25° C. to about 21° C. is done over a period of about 3 hours.

Preferably, the cooled suspension is further maintained for about 5 to about 18 hours.

The process for preparing form 9 may further comprise recovering the crystalline form from the suspension. The recovery may be done by any method known in the art, such as filtering, washing the filtered form and drying.

Figure 16:
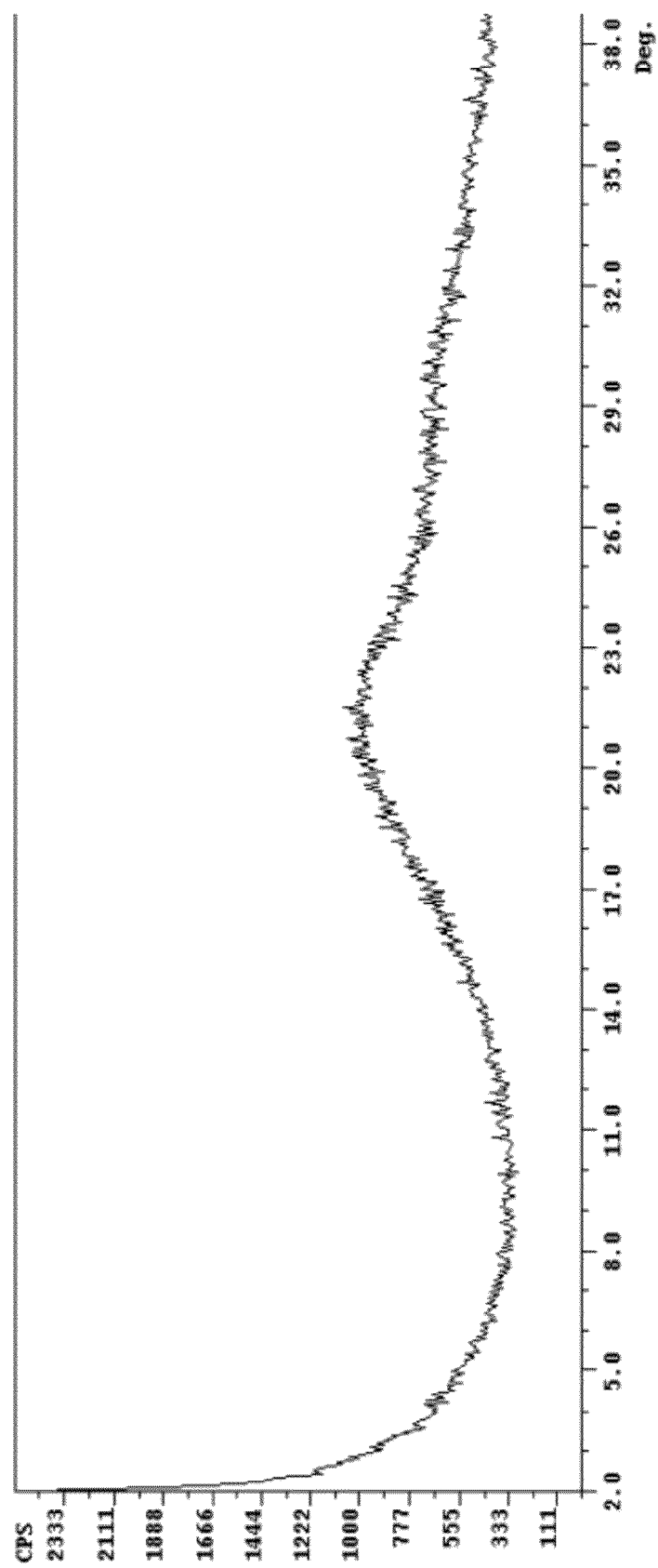
FIG. 16 shows the powder XRD of amorphous Tiotropium bromide.

The present invention provides amorphous form of Tiotropium bromide. The amorphous Tiotropium bromide may be substantially identified by the PXRD depicted in FIG. 16. The amorphous form of Tiotropium bromide may be with no more than about 10% of any other form of Tiotropium bromide, preferably with no more than about 5% of any other form of Tiotropium bromide, as measured by PXRD. Preferably, the amorphous form of Tiotropium bromide may be provided in a relatively pure form with no more than about 10% of Tiotropium bromide monohydrate, preferably with no more than about 5% of Tiotropium bromide monohydrate, as measured by PXRD.

The amorphous form of Tiotropium bromide is prepared by a process comprising lyophilizing a solution of Tiotropium bromide in water, t-butanol, methanol or mixtures thereof.

Typically, any form of Tiotropium bromide can be used as a starting material for the lyophilizing procedure. The methanolate forms of Tiotropium bromide, designated 1, 2, and 8, and the n-propanol solvate form of Tiotropium bromide, designated form 9, are preferred starting material for the above process. Preferably, the solution is prepared by dissolving Tiotropium bromide in water, in t-butanol, in methanol or in mixtures thereof. Preferably, the dissolution is performed at a temperature of from about 20° C. to about 40° C. The obtained solution may be filtered prior to lyophilizing it. Lyophilization may be done for about 24 to about 48 hours.

The present invention provides a process for preparing a crystalline form of Tiotropium bromide, designated form 3, characterized by a powder XRD pattern with peaks at about 9.82, 10.91, 13.45, 15.34, 17.93, 19.71, 20.90, and 21.45±0.2 degrees 2-theta, by a process comprising crystallizing Tiotropium bromide from a mixture comprising methanol and acetone at a ratio of about 3/1 (vol/vol), respectively.

The crystallization process comprising providing a solution of Tiotropium bromide in a mixture comprising methanol and acetone at a ratio of about 3/1 (vol/vol), respectively, and cooling the solution to obtain a suspension.

The solution is provided by combining Tiotropium bromide and a mixture comprising methanol and acetone at a ratio of about 3/1 (vol/vol), respectively, and heating.

Preferably, the heating is to a temperature of about 50° C. to about 70° C., more preferably, to a temperature of about 60° C.

Typically, the solution is cooled to induce precipitation of the crystalline form. Preferably, the cooling is to a temperature of about room temperature to about −5° C. Preferably, when the cooling is performed to a temperature lower than room temperature, that temperature is reached over a period of about 5 minutes.

Preferably, the suspension may be maintained for at least about 3 hours, to increase the yield of the crystalline form. The process for preparing form 3 may further comprise recovering the crystalline form from the suspension.

The process for preparing Form 3 may further comprise recovering form 3 from the suspension. The recovery may be done by any method known in the art, such as filtering, and drying under nitrogen for about 30 minutes, followed by further drying under reduced pressure for at least about 15 hours.

The present invention provides a process for preparing a crystalline form of Tiotropium bromide, designated form 10, characterized by a PXRD pattern with peaks at about 9.82, 10.88, 13.28, 15.27, 16.39, 17.96, 19.67, 20.71, and 21.30±0.2 degrees 2-theta by a process comprising crystallizing Tiotropium bromide from n-butanol.

The process comprises providing a solution of Tiotropium bromide in n-butanol, and cooling the solution to obtain a suspension.

The solution is provided by combining Tiotropium bromide and n-butanol, and heating. Preferably, the heating is done to a temperature ranging from about 90° C. to about 96° C., more preferably, the heating is done to a temperature of about 94° C. Preferably, heating to a temperature ranging from about 90° C. to about 96° C. is done for a period of about 2.5 to 3 hours. Optionally, the hot solution may be filtered prior to cooling it.

Usually, the solution is cooled to induce precipitation of the crystalline product. The solution is cooled, preferably to a temperature ranging from about 25° C. to about 20° C., more preferably, the solution is cooled to a temperature of about 22° C. Reaching the above temperature is done over a period of at least about 6 hours.

The obtained suspension is maintained to increase the yield of the crystallized product. Preferably, the suspension is maintained for at least about 5 hours.

The process for preparing crystalline form 10 can further comprise recovering it from the suspension. The recovery may be done by any method known in the art, such as filtering, washing the filtered form with n-butanol and drying.

The present invention provides a process for preparing a crystalline form of Tiotropium bromide, designated form 4, characterized by a powder XRD pattern with peaks at about 9.92, 11.03, 13.41, 15.31, 18.10, 19.91, 20.94, and 21.41±0.2 degrees 2-theta by a process comprising crystallizing Tiotropium bromide from ethanol.

Preferably, the process comprises providing a solution of Tiotropium bromide in ethanol, and cooling the solution to obtain a suspension.

The solution is provided by combining Tiotropium bromide and ethanol, and heating.

Preferably, the solution is heated to a temperature ranging from about 70° C. to about 80° C. More preferably, the heating is done at a temperature ranging from about 73° C. to about 78° C.

Typically, the solution is cooled to induce precipitation of the crystalline form. Preferably, the solution is cooled to room temperature. Preferably, the cooling to room temperature is performed over a period of about 5 hours. The obtained suspension is maintained for at least about 3 hours, to increase the yield of the crystallized product.

The process for preparing the above crystalline form may further comprise a process for recovering the said crystalline from the suspension. The recovery process may be done by any method known in the art, such as filtering, and drying under nitrogen for about 30 minutes, followed by further drying under reduced pressure for at least about 9 hours.

The present invention provides a process for preparing a crystalline form of Tiotropium bromide characterized by PXRD pattern with peaks at about 9.86, 10.97, 13.28, 15.28, 18.04, 19.80, 20.71, 21.26±0.2 degrees 2-theta by a process comprising crystallizing Tiotropium bromide from isopropanol.

The process comprises combining providing a solution of Tiotropium bromide in isopropanol, and cooling the solution to obtain a suspension The solution is provided by combining Tiotropium bromide and iso-propanol, and heating. Preferably, the heating is done to a temperature of from about 80° C. to about 100° C., more preferably, to about 81° C. Preferably, heating the isopropanol combination to a temperature from about 80° C. to about 100° C. is done for a period of about 5 hours. Optionally, the hot solution may be filtered, prior to cooling it.

Typically, the solution is cooled to induce precipitation of the crystalline. The solution is cooled, preferably to a temperature of from about 25° C. to about 21° C., more preferably, the solution is cooled to a temperature ranging from about 23° C. to about 25° C. Reaching the above temperature is done over a period of at least about 4 hours, preferably from about 4 hours to about 5 hours.

The obtained suspension is maintained to increase the yield of the crystallized product. Preferably, the suspension is maintained for at least about 5 hours.

The process for preparing the said crystalline form can further comprise recovering it from the suspension. The recovery may be done by any method known in the art, such as filtering, washing the filtered form and drying.

The present invention offers a process for producing the monohydrate form of Tiotropium bromide characterized by PXRD with peaks at about 8.9, 11.9, 13.5, 14.8, 16.7, 17.5, 20.3, 23.6, 24.1, and 26.9±0.2 degrees 2-theta by a process comprising providing a mixture of Tiotropium bromide in water.

The starting Tiotropium bromide can be any form of Tiotropium bromide. Any form of Tiotropium bromide refers to Tiotropium bromide solvate, anhydrous and amorphous. Typically, Tiotropium bromide solvate refers to any solvated form of Tiotropium bromide. Preferably, the solvate form of Tiotropium bromide is selected from a group consisting of: alcoholate and acetic acid solvate. Preferably, the alcoholate is any alcoholate solvate of Tiotropium bromide, more preferably, methanolate, ethanolate, n-propanol solvate, iso-propanolate, and n-butanolate, most preferably, n-propanol solvate and methanolate.

Preferably, the mixture is provided at room temperature. The process may comprise a step of maintaining the mixture at room temperature for about 4 to 8 hours.

The process for preparing the monohydrate may further comprise recovering the monohydrate from the mixture. The recovery may be done by a process comprising filtering the suspension, washing the filtered precipitate of the monohydrate form of Tiotropium bromide, and drying under a stream of nitrogen.

The novel forms of Tiotropium bromide, designated, 1, 2, 6, 7, 8, 9, 11, and amorphous can be micronized to prepare material suitable for formulation. Typically, the term "suitable for formulation" in reference to micronized Tiotropium bromide corresponds to Tiotropium bromide having at least 90% of the particles below 20 microns.

In one embodiment, the present invention provides micronized forms of Tiotropium bromide, designated 1, 2, 6, 7, 8, 9, 11, and amorphous. Typically, the term "micronized" refers to a substance wherein at least 90% of the particles have a particle size of less than 20 microns.

The micronization process can, optionally, be followed by a process comprising exposing the micronized form to a suitable solvent to restore the initial content of solvent in the solvate. Usually, the term "suitable solvent" corresponds to the kind of solvent in the original solvated form.

The present invention provides pharmaceutical formulations comprising at least one form of Tiotropium bromide, designated 1, 2, 6, 7, 8, 9, 11, or amorphous form, and a pharmaceutically acceptable excipient.

The present invention provides a process for preparing pharmaceutical formulations comprising at least one form of Tiotropium bromide, designated 1, 2, 6, 7, 8, 9, 11, or amorphous form, and a pharmaceutically acceptable excipient.

The present invention provides pharmaceutical formulations comprising at least one form of Tiotropium bromide, designated 1, 2, 3, 4, 6, 7, 8, 9, 10, 11 or amorphous form, prepared according to the processes of the present invention, and a pharmaceutically acceptable excipient.

The present invention provides a process for preparing pharmaceutical formulations comprising at least one form of Tiotropium bromide, designated Forms 1, 2, 3, 4, 6, 7, 8, 9, 10, 11, or amorphous form, prepared according to the processes of the present invention, and a pharmaceutically acceptable excipient.

The present invention provides pharmaceutical formulations comprising at least one form of micronized Tiotropium bromide, designated 1, 2, 6, 7, 8, 9, 11, or amorphous, and a pharmaceutically acceptable excipient.

The present invention provides a process for preparing pharmaceutical formulations comprising at least one form of micronized Tiotropium bromide, designated 1, 2, 6, 7, 8, 9, 11, or amorphous, and a pharmaceutically acceptable excipient.

The present invention provides pharmaceutical formulations comprising at least one form of micronized Tiotropium bromide, designated 1, 2, 3, 4, 6, 7, 8, 9, 10, 11, or amorphous prepared according to the processes of the present invention, and a pharmaceutically acceptable excipient.

The present invention provides a process for preparing pharmaceutical formulations comprising at least one form of micronized Tiotropium bromide, designated Forms 1, 2, 3, 4, 6, 7, 8, 9, 10, 11, or amorphous, prepared according to the processes of the present invention, and a pharmaceutically acceptable excipient.

The compositions of the invention include powders, granulates, aggregates and other solid compositions comprising any one of the designated Forms of Tiotropium bromide.

In addition, the solid formulations comprising the above forms of Tiotropium bromide of the present invention may further include diluents, such as cellulose-derived materials like powdered cellulose, microcrystalline cellulose, microfine cellulose, methyl cellulose, ethyl cellulose, hydroxyethyl cellulose, hydroxypropyl cellulose, hydroxypropylmethyl cellulose, carboxymethyl cellulose salts and other substituted and unsubstituted celluloses; starch; pregelatinized starch; inorganic diluents like calcium carbonate and calcium diphosphate and other diluents known to the pharmaceutical industry. Yet other suitable diluents include waxes, sugars and sugar alcohols like mannitol and sorbitol, acrylate polymers and copolymers, as well as pectin, dextrin and gelatin.

Further excipients that are suitable in the present invention include binders, such as acacia gum, pregelatinized starch, sodium alginate, glucose and other binders used in wet and dry granulation and direct compression tableting processes. Excipients that also may be present in a solid formulation of the above forms of Tiotropium bromide further include disintegrants like sodium starch glycolate, crospovidone, low-substituted hydroxypropyl cellulose, and others. In addition, excipients may include tableting lubricants like magnesium and calcium stearate and sodium stearyl fumarate; flavorings; sweeteners and preservatives.

The formulations may be administered orally, parenterally, (including subcutaneous, intramuscular, and intravenous), by inhalation and ophthalmogically. Although the most suitable route in any given case will depend on the nature and severity of the condition being treated, the most preferred route of the present invention is oral. Dosages may be conveniently presented in unit dosage form and prepared by any of the methods well-known in the art of pharmacy.

Dosage forms include solid dosage forms, like tablets, powders, capsules, suppositories, sachets, troches and losenges as well as liquid suspensions and elixirs. While the description is not intended to be limiting, the invention is also not intended to pertain to true solutions of Tiotropium bromide whereupon the properties that distinguish the solid forms of Tiotropium bromide are lost. However, the use of the novel forms to prepare such solutions (e.g. so as to deliver, in addition to Tiotropium bromide, a solvate to said solution in a certain ratio with a solvate) is considered to be within the scope of the invention.

Capsule dosages, of course, will contain the solid composition within a capsule which may be made of gelatin or other conventional encapsulating material. Tablets and powders may be coated. Also, tablets and powders may be coated with an enteric coating. The enteric coated powder forms may have coatings including, but not limited to, phthalic acid cellulose acetate, hydroxypropylmethyl-cellulose phthalate, polyvinyl alcohol phthalate, carboxymethylethylcellulose, a copolymer of styrene and maleic acid, a copolymer of methacrylic acid and methyl methacrylate, and like materials, and if desired, they may be employed with suitable plasticizers and/or extending agents. A coated tablet may have a coating on the surface of the tablet or may be a tablet comprising a powder or granules with an enteric-coating.

One skilled in the art would appreciate that there is a typical small analytical error involved in PXRD measurements, generally of the order of about ±0.2 degrees 2-theta, or less, for each peak. Accordingly, PXRD peak data herein are presented in the form of "a PXRD pattern with peaks at A, B, C, etc.±0.2 degrees 2-theta." This indicates that, for the crystalline form in question, the peak at A could, in a given instrument on a given run, appear somewhere between A±0.2 degrees 2-theta, the peak at B could appear at B±0.2 degrees 2-theta, etc. Such small, unavoidable uncertainty in the identification of individual peaks does not translate into uncertainty with respect to identifying individual crystalline forms since it is generally the particular combination of peaks within the specified ranges, not any one particular peak, that serves to unambiguously identify crystalline forms. In an alternative, the present invention provides the overall pattern which can also be used independently of the reported peak positions or peak heights.

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

Instruments and reagents utilized include:

EXAMPLES

Instrument: Agilent Technologies Mod. 6850 gas chromatograph
Column: DB-WAX, 30 m, 0.32 mm ID, 0.5 μm df
Detector: FID

| Temperature | 300° C. |
| Hydrogen flow | 30.0 mL/min |
| Air flow | 300.0 mL/min |
| Makeup | Helium; 30.0 mL/min (total flow) |

Inlet:

| Mode | Splitless |
| Temperature | 140° C. |
| Pressure | 9.00 psi |
| Gas type | Helium |
| Purge flow | 60.0 mL/min |
| Purge time | 0.10 min |
| Total flow | 64.6 mL/min |
| Injection volume | 1.0 μL |

Oven:

| Initial temperature | | 40° C. | |
| Initial time | | 5.00 min | |
| Ramps # | Rate (° C./min) | Final temp(° C.) | Final time |
| --- | --- | --- | --- |
| 1 | 10.00 | 230 | 7.00 |
| 2 | 0.0 | | |
| Run time | 31.00 min | | |

Wash Solvent: Dimethylsulphoxide
Check for:
Disopropylether, n-Heptane, Acetone, Methanol, Dichloromethane, Ethanol, Acetonitrile, Acetic Acid.
Internal Standard Solution:
250 μL Dioxane→250 mL Dimethylsulphoxide.
Stock Standard Solution:
1 mL of each solvent to 100.0 mL with Internal Standard Solution.
Working Standard Solution:
1 mL Stock Standard Solution to 100.0 mL with Internal Standard Solution (0.1 μL/mL each solvent).
Sample Solution:
To 100 mg of Sample add 1 mL of Internal Standard Solution.
Powder X-Ray Diffraction:
Powder X-ray diffraction ("PXRD") analysis using an ARL X-ray powder diffractometer model XTRA-030, equipped with Peltier detector, and an X-ray source of Cu Kα radiation, wavelength: 1.54178 Å. The sample was introduced using round standard aluminum sample holder with round zero background quartz plate. Scanning parameters: Range: 2-40 deg. 2 θ, continuous Scan, Rate: 3 deg./min. The accuracy of peak positions is defined as +/−0.2 degrees due to experimental differences like instrumentations, sample preparations etc. . . . .

Single Crystal XRD Method for Analysis of Tiotropium Bromide n-Propanol Solvate:
Data were collected on Xcalibur PX, Cu Kα using combined ϕ and ω scans. All non-hydrogen atoms were refined anisotropically, hydrogen atoms were refined riding in expected geometric positions, OH hydrogen atoms were located from fourier maps. Data collection: CrysAlis RED (Oxford Diffraction, 2002); cell refinement: CrysAlis RED; data reduction: CrysAlis RED; program used to solve structure: SIR92 (Altomare et al., 1994); program used to refine structure: CRYSTALS (Betteridge et al., 2003)
Thermal Gravimetric Analysis ("TGA")
TGA/SDTA 851, Mettler Toledo, Sample weight 7-15 mg. Heating rate: 10° C./min., in $N_2$ stream: flow rate: 50 ml/min. Scan range: 30-250° C.
Differential Scanning calorimetry ("DSC")
DSC 822$^e$/700, Mettler Toledo, Sample weight: 3-5 mg. Heating rate: 10° C./min., Number of holes of the crucible: 3
In $N_2$ stream: flow rate=40 ml/min
Scan range: 30-250° C., 10° C./minutes heating rate.

Example 1

Preparation of Tiotropium Bromide Form 1

Tiotropium bromide (2.50 g) was dissolved at 57° C. with a mixture 1/3 (V/V) of methanol/acetone (55 ml). The solution was heated to 57° C. for about 30 min., and then, cooled to 21° C. in at least 3 hours (no solid formation observed) and was quickly cooled to −10° C. in about 5 min. The obtained suspension was maintained at −10° C. for at least 3 hours, and filtered on a sintered glass funnel and the solid was washed with 1.0 mL of the mixture. Drying for 30 min. at 21° C. under $N_2$ flow and then for 7 hours at 111° C. under reduced pressure (40 mbar), yielded 0.01 g of Tiotropium bromide Form 1.

Example 2

Preparation of Tiotropium Bromide Form 2

Tiotropium bromide (2.50 g) was dissolved at 60° C. with a mixture 3/1 (V/V) of methanol/acetone (13 ml). The solution was heated to 60° C. for about 30 min and then cooled to 22° C. in at least 3 hours. The obtained suspension was maintained at 22° C. for at least 2 hours, and filtered on a sintered glass funnel and the solid was washed two times with 1.5 mL of the mixture. Drying for 30 min. at 22° C. under $N_2$ flow and then for 7 hours at 111° C. under reduced pressure (40 mbar), yielded 1.19 g of Tiotropium bromide Form 2. TGA weight loss: 2.3%.

Example 3

Preparation of Tiotropium Bromide Form 2

Tiotropium bromide (1.00 g) was dissolved at 60° C. with a mixture 1/1 (V/V) of methanol/acetone (8.5 ml). The solution was heated to 60° C. for about 30 min. and then cooled to 21° C. in at least 3 hours. The obtained suspension was maintained at 21° C. for at least 3 hours, and filtered on a sintered glass funnel and the solid was washed three times with 1.0 mL of the mixture. Drying for 30 min. at 21° C. under $N_2$ flow and then for 7 hours at 111° C. under reduced pressure (40 mbar), yielded 0.154 g of Tiotropium bromide Form 2. TGA weight loss: 0.8%.

Example 4

Preparation of Tiotropium Bromide Characterized by a Powder XRD Pattern with Peaks at about 9.82, 10.91, 13.45, 15.34, 17.93, 19.71, 20.90, and 21.45±0.2 Degrees 2-Theta Crude Tiotropium bromide (2.50 g) was dissolved at 60° C. with a mixture 3/1 (V/V) of methanol/acetone (13 ml). The solution was heated to 60° C. for about 30 min and then was cooled to 22° C. in at least 3 hours. The obtained suspension was maintained at 22° C. for at least 2 hours, and filtered on a sintered glass funnel and the solid was washed two times with 1.5 mL of the mixture. Drying for 30 min. at 22° C. under $N_2$ flow yielded 1.40 g of Tiotropium bromide Form 3. TGA weight loss: 5.1%.

Example 5

Preparation of Tiotropium Bromide Characterized by a Powder XRD Pattern with Peaks at about 9.82, 10.91, 13.45, 15.34, 17.93, 19.71, 20.90, and 21.45±0.2 Degrees 2-Theta Crude Tiotropium bromide (2.50 g) was dissolved at 60° C. with a mixture 3/1 (V/V) of methanol/acetone (13 ml). The solution was heated to 60° C. for about 30 min and then was cooled to 22° C. in at least 3 hours. The obtained suspension was maintained at 22° C. for at least 2 hours, and filtered on a sintered glass funnel and the solid was washed two times with 1.5 mL of the mixture. Drying for 30 min. at 22° C. under $N_2$ flow and then for 15 hours at 60° C. under reduced pressure, yielded 1.33 g of Tiotropium bromide Form 3. TGA weight loss: 4.3%.

Example 6

Preparation of Tiotropium Bromide Characterized by a Powder XRD Pattern with Peaks at about 9.82, 10.91, 13.45, 15.34, 17.93, 19.71, 20.90, and 21.45±0.2 Degrees 2-Theta Crude Tiotropium bromide (2.50 g) was dissolved at 60° C. with a mixture 3/1 (V/V) of methanol/acetone (13 ml). The solution was heated to 60° C. for about 30 min., was quickly cooled to −5° C. (5 min.) and maintained at −5° C. for at least 3 hours. The obtained suspension was filtered on a sintered glass funnel and the solid was washed with 1.0 mL of the mixture. Drying for 30 min. at 21° C. under $N_2$ flow yielded 1.31 g of Tiotropium bromide Form 3. TGA weight loss: 4.5%.

Example 7

Preparation of Tiotropium Bromide Characterized by a Powder XRD Pattern with Peaks at about 9.92, 11.03, 13.41, 15.31, 18.10, 19.91, 20.94, and 21.41±0.2 Degrees 2-Theta Crude Tiotropium bromide (1.00 g) was dissolved in absolute ethanol (65 ml) at 78° C. The solution was heated to 78° C. for about 30 min and then was cooled to 22° C. in at least 6 hours. The obtained suspension was maintained at 22° C. for at least 3 hours, and filtered on a sintered glass funnel and the solid was washed two times with absolute ethanol (2×1.0 ml). Drying for 30 min. at 22° C. under $N_2$ flow and then for 9 hours at 60° C. under reduced pressure (17 mbar), yielded 0.66 g of Tiotropium bromide Form 4. TGA weight loss: 4.8%. Stoichiometric value of hemi-ethanolate: 4.64%.

Example 8

Preparation of Tiotropium Bromide Characterized by a Powder XRD Pattern with Peaks at about 9.92, 11.03, 13.41, 15.31, 18.10, 19.91, 20.94, and 21.41±0.2 Degrees 2-Theta Crude Tiotropium bromide (0.80 g) was dissolved in ethanol 96% (18.4 ml) at 73° C. The solution was heated to 73° C. for about 1 hour and then was cooled to 23° C. in at least 5 hours. The obtained suspension was maintained at 23° C. for at least 3 hours, and filtered on a sintered glass funnel and the solid was washed two times with ethanol 96% (2×1.5 ml). Drying for 1.5 hours at 23° C. under $N_2$ flow and for 5 hours at 60° C. under reduced pressure (18 mbar), yielded 0.39 g of Tiotropium bromide Form 4. TGA weight loss: 4.7%. Stoichiometric value of hemi-ethanolate: 4.64%.

Example 9

Preparation of Tiotropium Bromide Form 6

Tiotropium bromide (1.00 g) was dissolved at 45° C. with a mixture 7/2 (V/V) of acetic acid/methanol (11 ml), the solution was heated to 45° C. for 1.5 hours and n-heptane (2.75 ml) was then added drop-wise in at least 20 min. The obtained solution was heated to 45° C. for one hour (no solid formation observed), was cooled to 23.5° C. in at least 3 hours and the suspension was maintained at 23.5° C. for at least 3 hours. After filtration on a sintered glass funnel, the solid was washed three times with 3.0 mL of n-heptane. Drying for 16 hours at 60° C. under reduced pressure (18 mbar), yielded 0.67 g of Tiotropium bromide Form 6. TGA weight loss: 5.4%.

Example 10

Preparation of Tiotropium Bromide Form 6

Tiotropium bromide (0.50 g) was dissolved at 45° C. with a mixture 7/1 (V/V) of acetic acid/methanol (10 ml), the solution was heated to 45° C. for 1.5 hours and n-heptane (2.5 ml) was then added drop-wise in at least 15 min. The obtained solution was heated to 45° C. for 0.5 hour (no solid formation observed), was cooled to 28° C. in at least 3 hours and the suspension was maintained at 28° C. for at least 3 hours. After filtration on a sintered glass funnel, the solid was washed three times with 2.0 mL of n-heptane. Drying for 18 hours at 60° C. under reduced pressure (19 mbar) or for 7 hours at 90-100° C. at 18 mbar pressure yielded 0.29 g of Tiotropium bromide Form 6. TGA weight loss: 5.7%.

Example 11

Preparation of Tiotropium Bromide Form 7

Tiotropium bromide (0.60 g) was dissolved at 45° C. with a mixture 1/4 (V/V) of acetic acid/acetonitrile (6.75 ml), the solution was heated to 45° C. for one hour and diisopropylether (DIPE) (6.75 ml) was then added drop-wise in at least 15 min. The obtained suspension was heated to 45° C. for at least one hour, was cooled to 21.5° C. in at least 3 hours and was maintained at 21.5° C. for at least 3 hours. After filtration on a sintered glass funnel, the solid was washed three times with 1.8 mL of diisopropylether (DIPE). Drying for one hour at 21° C. under $N_2$ flow, yielded 0.40 g of Tiotropium bromide Form 7.

Example 12

Preparation of Tiotropium Bromide Form 8

Tiotropium bromide (0.80 g) was dissolved in methanol (3.4 ml) at 63° C. The solution was heated to 63° C. for about 1 hour and then was cooled to 22° C. in at least 2 hours. The obtained suspension was maintained at 22° C. for at least 3.5 hours, and filtered through a sintered glass funnel. The solid was washed two times with methanol (2×0.8 ml), and dried for 1 hour at 22° C. under $N_2$ flow, yielding 0.49 g of tiotropium bromide Form 8. TGA weight loss: 5.1%.

Example 13

Preparation of Tiotropium Bromide Form 9

Tiotropium bromide (45 mg) was dissolved at 97° C. in n-propanol (4 ml). Then amylacetate (4 ml) was added to the hot solution of Tiotropium bromide in n-propanol. Crystallisation for 5 days at isothermal conditions at 25° C. provided single crystals of tiotropium bromide Form 9. Single crystal was trapped by sticky glue technique from the mother liquor on the top of a glass needle of the goniometer assembly and measured at 298 K.

Example 14

Preparation of Tiotropium Bromide

Tiotropium bromide (0.40 g) was dissolved in isopropanol (160 ml) at 81° C. The solution was heated to 81° C. for about 5 hour, filtered through a sintered glass funnel and then cooled to 23° C. in at least 4 hours. The obtained suspension was maintained at 23° C. for at least 5 hours, and filtered through a sintered glass funnel. The solid was washed two times with isopropanol (2×1.0 ml), and dried for 1 hour at 23° C. under $N_2$ flow and then for 5 hours at 60° C. under reduced pressure (18 mbar), yielding 0.23 g of tiotropium bromide. TGA weight loss: 6.0%.

Example 15

Preparation of Tiotropium Bromide Form 12

Tiotropium bromide (4 g) was dissolved at 97° C. in n-propanol (348 ml), then cooled to 55° C. in 4 h and from 55° C. to 25° C. in 3 h. After stirring for 12 h at 20-25° C. the suspension was filtered, dried at 45° C. for 20 h under reduced pressure and tiotropium bromide form 12 (3 g) were obtained.

Example 16

Preparation of Tiotropium Bromide Form 12

Tiotropium bromide (2 g) was dissolved at 83° C. in n-propanol containing 5% w/w water (60 ml), then cooled to 25° C. in 4 h. After stirring for 12 h at 20-25° C. the suspension was filtered, dried at 45° C. for 20 h under reduced pressure and tiotropium bromide form 12 (1.3 g) was obtained.

Example 17

Preparation of Tiotropium Bromide Form 12

Tiotropium bromide (2 g) was dissolved at 85° C. in n-propanol containing 2% w/w water (58.5 ml), then cooled to 25° C. in 5 h. After stirring for 12 h at 20-25° C. the suspension was filtered, dried at 45° C. for 20 h under reduced pressure and tiotropium bromide form 12 (1.8 g) was obtained.

Example 18

Preparation of Tiotropium Bromide Characterized by a PXRD Pattern with Peaks at about 9.82, 10.88, 13.28, 15.27, 16.39, 17.96, 19.67, 20.71, and 21.30±0.2 Degrees 2-Theta Crude tiotropium bromide (0.40 g) was dissolved in n-butanol (70 ml) at 94° C. The solution was heated to 94° C. for about 2.5 hour, filtered through a sintered glass funnel and then cooled to 22° C. in at least 6 hours. The obtained suspension was maintained at 22° C. for at least 5 hours, and filtered through a sintered glass funnel. The solid was washed two times with n-butanol (2×1.0 ml), and dried for 3 hour at 22° C. under $N_2$ flow and then for 16.5 hours at 65° C. under reduced pressure (18 mbar), yielding 0.133 g of tiotropium bromide Form 10. TGA weight loss: 6.9%.

Example 19

Preparation of Tiotropium Bromide Form 11

Tiotropium bromide methanolate, hemi-n-buthanolate and hemi-acetic acid solvate were heated in separate glass containers in an oven at 160° C. for 1 hour, then each substance was measured by XRD.

Example 20

Preparation of Amorphous Form of Tiotropium Bromide 1 g of Tiotropium bromide was dissolved at room temperature in 50 ml of water, it was then filtered (to get rid of small unsoluble particles) and put to lyophilization for 24 hours.
chamber vacuum: <20 μm Hg
chamber temperature during 24 hours: from −40° C. to 22° C.

Example 21

General Procedure for Preparing Tiotropium Bromide Monohydrate

Tiotropium bromide is mixed with 80.7 mL of water and the mixture is stirred at r.t. for 4 h. The mixture is filtered and washed with 10 mL of water. The product is left on the filter under vacuum and under nitrogen at r.t. for 15 min, providing the monohydrate form.

Example 19

Preparation of Tiotropium Bromide Monohydrate

Tiotropium was suspended in water and the suspension was stirred at 22-25° C. for 4 h. After that it was filtered and the solid was washed with 10 mL of water. The product was left on the filter under vacuum and under nitrogen at 20°-25° C. for 15'. The content of water on the sample was 4.3% (TGA analysis).

Example 20

Preparation of Tiotropium Bromide Monohydrate from Tiotropium Bromide Ethanolate 13.45 g of dry Tiotropium bromide ethanolate were suspended in 80.7 mL of water and the suspension was stirred at r.t. for 4 h. After it was filtered washing with 10 mL of water was conducted. The product was left on the filter under vacuum and under nitrogen at r.t. for 15 min. 11.66 g of monohydrate were obtained. The content of water on the sample was 4.3% (TGA analysis).

Example 21

Micronization of Tiotropium Bromide

Tiotropium Bromide was micronized to obtain P.S.D target of:
Min. 80%<5.84 μm
Min. 70% between 0.6 and 10 microns
The micronizer in use was a Jet-mill MC 50 (made by Micro-Macinazionne). 32°05' angle nozzles were installed.
Nitrogen was used as the micronization gas.
Micronization air Pressure was 10 bars.
Feed rate was 0.2 kg/hr.
The micronized Tiotropium bromide obtained by the above process has a PSD value:
80%≤5.84 μm
93.76% between 0.6 and 10 microns.

Figure 14:
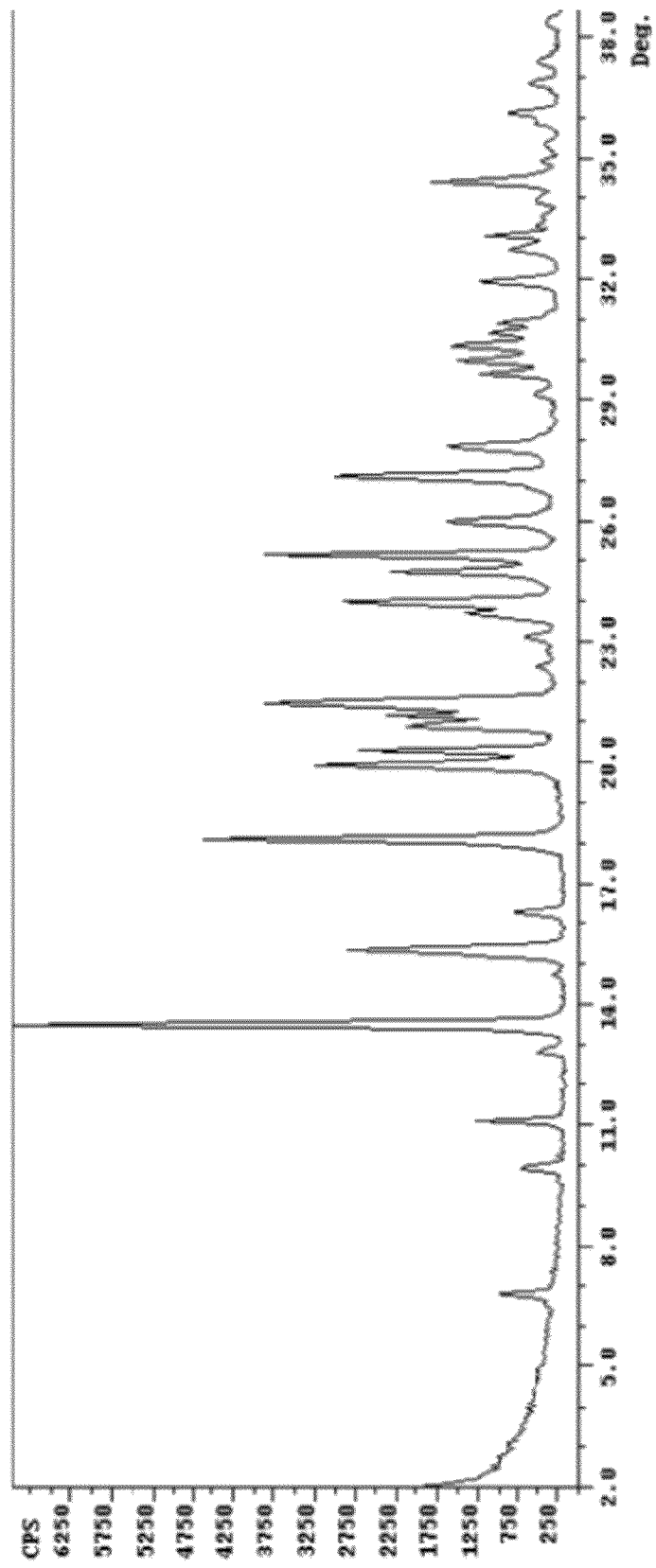
FIG. 14 shows the powder XRD pattern of Tiotropium bromide Form 12.
Figure 15:
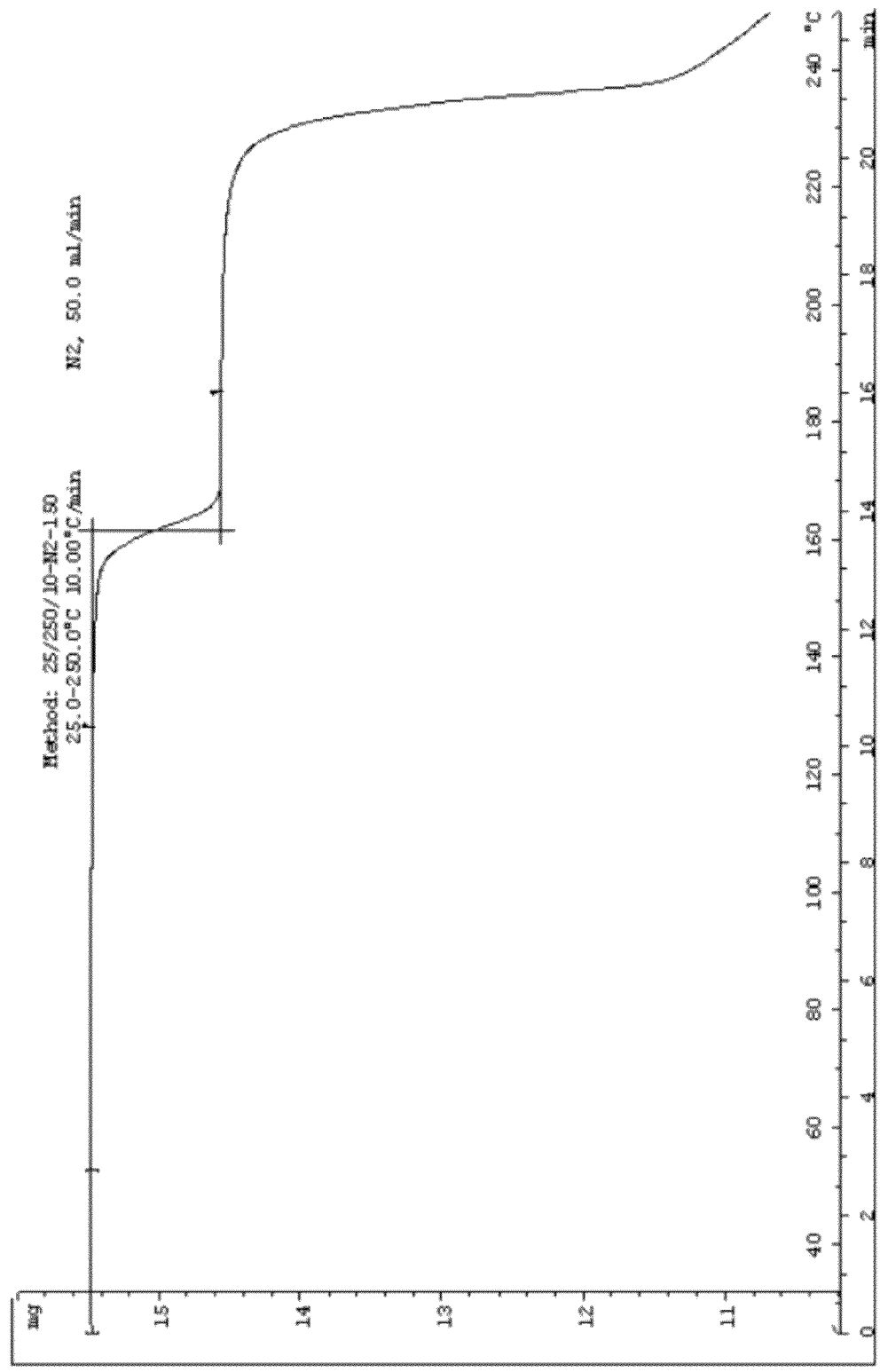
FIG. 15 shows the TGA curve of Tiotropium bromide Form 12.

What is claimed is:

1. A crystalline hemi-n-propanol solvate of tiotropium bromide characterized by a PXRD pattern as depicted in FIG. 14.

2. The crystalline tiotropium bromide of claim 1, further characterized by weight loss of about 5.9% at a temperature of about 125° C. to about 184° C. by TGA.

3. The crystalline tiotropium bromide of claim 1, further characterized by a DSC thermogram having a first endothermic peak at 158° C., and a second endothermic peak at about 229° C.

4. A micronized form of Tiotropium bromide, according to claim 1.

5. A pharmaceutical formulation comprising the form of Tiotropium bromide according to claim 1, and a pharmaceutically acceptable excipient.

6. A pharmaceutical formulation comprising micronized Tiotropium bromide of claim 4, and a pharmaceutically acceptable excipient.

* * * * *